(12) United States Patent
Fujimoto et al.

(10) Patent No.: US 8,213,083 B2
(45) Date of Patent: Jul. 3, 2012

(54) WAVELENGTH SELECTION FILTER, FILTER UNIT, LIGHT SOURCE DEVICE, OPTICAL APPARATUS, AND REFRACTIVE INDEX SENSOR

(75) Inventors: Masahiro Fujimoto, Yokohama (JP); Hideaki Hirai, Yokohama (JP); Manabu Seo, Yokohama (JP)

(73) Assignee: Ricoh Company, Ltd., Tokyo (JP)

( * ) Notice: Subject to any disclaimer, the term of this patent is extended or adjusted under 35 U.S.C. 154(b) by 305 days.

(21) Appl. No.: 12/510,448

(22) Filed: Jul. 28, 2009

(65) Prior Publication Data

US 2010/0020401 A1 Jan. 28, 2010

(30) Foreign Application Priority Data

Jul. 28, 2008 (JP) ................... 2008-192942

(51) Int. Cl.
*G02B 5/18* (2006.01)
(52) U.S. Cl. ....................................................... 359/571
(58) Field of Classification Search .................. 359/571, 359/572, 576; 372/20; 398/84, 87
See application file for complete search history.

(56) References Cited

U.S. PATENT DOCUMENTS

| | | | | |
|---|---|---|---|---|
| 5,377,044 A | * | 12/1994 | Tomono et al. | 359/566 |
| 5,880,882 A | * | 3/1999 | Michel et al. | 359/436 |
| 6,002,522 A | * | 12/1999 | Todori et al. | 359/573 |
| 2002/0063962 A1 | | 5/2002 | Takada et al. | |
| 2006/0018021 A1 | | 1/2006 | Tomkins et al. | |

FOREIGN PATENT DOCUMENTS

| | | |
|---|---|---|
| EP | 1 674 895 A1 | 6/2006 |
| EP | 1 862 827 A1 | 12/2007 |
| JP | 58-198007 A | 11/1983 |
| JP | 2002-258034 A | 9/2002 |
| JP | 3711446 B2 | 8/2005 |
| JP | 2005-275089 A | 10/2005 |
| JP | 2005-275092 A | 10/2005 |
| JP | 2006-349776 A | 12/2006 |
| JP | 2007-232456 A | 9/2007 |
| JP | 2008-8990 A | 1/2008 |
| WO | WO 98/57200 A1 | 12/1998 |
| WO | WO 01/27666 A2 | 4/2001 |

OTHER PUBLICATIONS

Mashev et al., "Zero Order Anomaly of Dielectric Coated Gratings," Optics Communications, vol. 55, No. 6, pp. 377-380, Oct. 15, 1985.

\* cited by examiner

*Primary Examiner* — Stephone Allen
*Assistant Examiner* — Kimberly N Kakalec
(74) *Attorney, Agent, or Firm* — Dickstein Shapiro LLP

(57) ABSTRACT

A wavelength selection filter selectively resonating and reflecting light of a given wavelength contained in incident light, includes a substrate having a rectangular waveform concave and convex structure which is formed on a plane on which the incident light falls incident, the concave and convex structure including convex portions and concave portions which are arranged in one axial direction and a multilayer structure including a first layer and a second layer respectively coating one and the other one of side surfaces, in the one axial direction, of each of convex portions of the concave and convex structure. A refractive index of the first layer and a refractive index of the second layer are both higher than a refractive index of the substrate.

10 Claims, 25 Drawing Sheets

FIG. 46

| Wavelength selection filter | Resonant wavelength (nm) | P (nm) | Form of concave and convex structure | d (nm) | Film thickness (nm) | | | | Refractive index | | | | Half-width of peak waveform (nm) | Half-width of incident angle (deg) |
|---|---|---|---|---|---|---|---|---|---|---|---|---|---|---|
| | | | | | t0 | t1 | t2 | t3 | n0 | n1 | n2 | n3 | | |
| 101 | 605 | 400 | Rectangular waveform | 100 | 100 | 100 | 100 | 100 | 1.46 | 2.12 | 2.12 | 1 | 7.1(1.2%) | 3.0 |
| 201 | 623 | 400 | Rectangular waveform | 200 | 100 | 100 | 100 | 100 | 1.46 | 2.12 | 2.12 | 1 | 3.7(0.6%) | 3.2 |
| 301 | 630 | 400 | Rectangular waveform | 200 | 100 | 100 | 100 | 100 | 1.46 | 2.12 | 2.12 | 1.25 | 0.7(0.1%) | 1.4 |
| Conventional example | 623.4 | | Triangular waveform | | | | | | 1.5 | 2.25 | 2.25 | 1 | 0.08 | 0.05 |

WAVELENGTH SELECTION FILTER, FILTER UNIT, LIGHT SOURCE DEVICE, OPTICAL APPARATUS, AND REFRACTIVE INDEX SENSOR

CROSS REFERENCE TO RELATED APPLICATIONS

The present application is based on and claims priority from Japanese Application Number 2008-192942, filed on Jul. 28, 2008, the disclosure of which is hereby incorporated by reference herein in its entirety.

BACKGROUND OF THE INVENTION

1. Field of the Invention

The present invention relates to a wavelength selection filter, a filter unit, a light source device, an optical apparatus and a refractive index sensor, and more specifically to a wavelength selection filter for selectively resonating and reflecting light of a given wavelength contained in incident light, a filter unit having the wavelength selection filter, a light source device having the wavelength selection filter or the filter unit, an optical apparatus including the light source device, and a refractive index sensor having the wavelength selection filter.

2. Description of the Related Art

An optical system or an optical apparatus may require a light beam of a given wavelength alone from a light bundle in which multiple light beams of different wavelengths are mixed together. In this instance, a wavelength selection filter (also called a wavelength filter) is generally used.

Japanese Patent No. 3711446, for example, discloses a wavelength filter including a substrate having fine concave and convex portions at its surface, and a dielectric layer coating the surface having the fine concave and convex portions. In this wavelength filter, the fine concave and convex portions and the dielectric layer form a waveguide layer for light incident on the surface.

Also, Japanese Patent Application Publication No. 2005-275089 discloses a tunable wavelength selection filter that selectively reflects light of a given wavelength, which meets a resonance condition, in incident light as reflected light.

Moreover, Japanese Patent Application Publication No. 2007-232456 discloses a refractive index sensor for detecting the refractive index of an object to be measured.

However, the wavelength filter disclosed in Japanese Patent No. 3711446 has the disadvantage that deviation of the incidence angle of light from a designed value leads to a decrease in the amount of light of a given wavelength reflected by the wavelength filter. Further, the wavelength filter disclosed in Japanese Patent No. 3711446 poses the possibility that the deviation of the incident angle of light from the designed value may lead to reflection of light of multiple wavelengths different from the given wavelength.

Also, the tunable wavelength selection filter disclosed in Japanese Patent Application Publication No. 2005-275089 has the disadvantages of having difficulty in fabrication since fine electrodes have to be formed on a substrate, and also having difficulty in low-cost fabrication since a special material has to be used for a waveguide layer.

SUMMARY OF THE INVENTION

The present invention has been made in view of such circumstances. An object of the present invention is to provide a wavelength selection filter having enhanced wavelength selectivity and a wide allowable range of the incident angle of light.

In order to attain the above object, an embodiment of the present invention provides a wavelength selection filter selectively resonating and reflecting light of a given wavelength contained in incident light, including: a substrate being formed on a plane on which the incident light falls incident, and having a concave and convex structure in a rectangular waveform in one axial direction; and a multilayer structure including a first layer and a second layer respectively coating one and the other one of side surfaces, in the one axial direction, of each of convex portions of the concave and convex structure. In the wavelength selection filter, a refractive index of the first layer and a refractive index of the second layer are both higher than a refractive index of the substrate.

BRIEF DESCRIPTION OF THE DRAWINGS

FIG. 46 is a table for explaining differences among the wavelength selection filters;

DETAILED DESCRIPTION OF THE PREFERRED EMBODIMENTS

Figure 1:
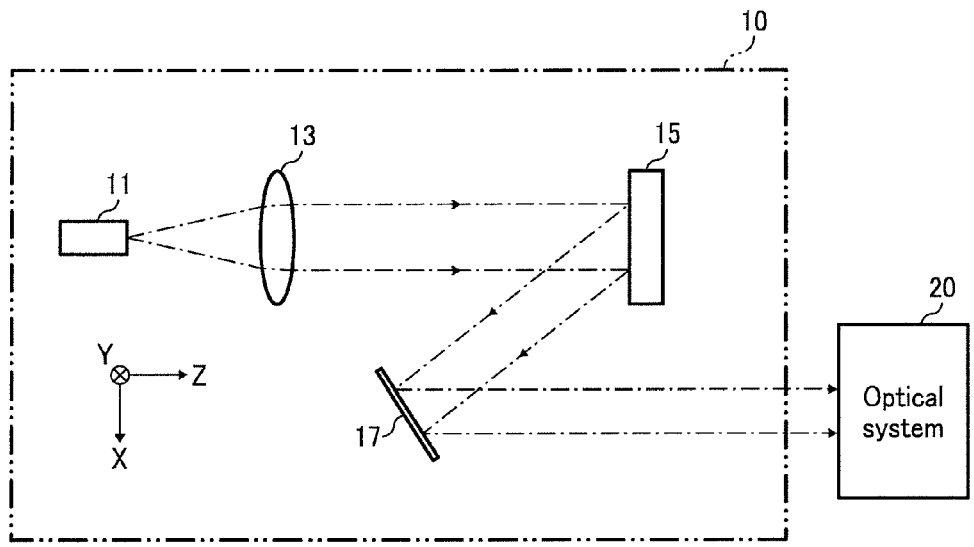
FIG. 1 is a schematic diagram of a light source device according to an embodiment of the present invention.

An embodiment of the present invention will be described below with reference to FIGS. 1 to 26. FIG. 1 shows a light source device 10 including a wavelength selection filter 101 according to an embodiment of the present invention.

The light source device 10 includes a light source 11, an optical element 13 such as a coupling lens, a filter unit 15 such as an optical filter unit, a reflecting mirror 17, and the like. The filter unit 15 may receive the light bundle transmitted through the optical element. A light beam reflected by the wavelength selection filter 101 of the filter unit is outputted.

The light source 11 outputs a light bundle in which multiple light beams of different wavelengths are mixed together.

The coupling lens 13 substantially collimates the light bundle from the light source 11. Incidentally, in an XYZ three-dimensional orthogonal coordinate system in the description herein, the direction of the optical axis of the coupling lens 13 is regarded as the Z-axis direction.

The optical filter unit 15 receives the substantially collimated light bundle having passed through the coupling lens 13, and reflects only a light beam lying within a given wavelength range. Details of the optical filter unit 15 will be described later.

The reflecting mirror 17 is disposed on an optical path of the light beam reflected from the optical filter unit 15, and reflects the light beam in a positive Z (+Z) direction. The light beam reflected from the reflecting mirror 17 is outputted from the light source device 10. In other words, the light source device 10 outputs the light beam within the given wavelength range, as the substantially collimated light beam.

Then, the light beam outputted from the light source device 10 is guided to an optical system 20 optimized for the light beam within the given wavelength range. Incidentally, optical apparatuses 30 including the light source device 10 and the optical system 20 include an analysis apparatus, a test apparatus, and a measurement apparatus, all of which utilize light lying within a given wavelength range.

Description will now be given of the optical filter unit 15.

Figure 2:
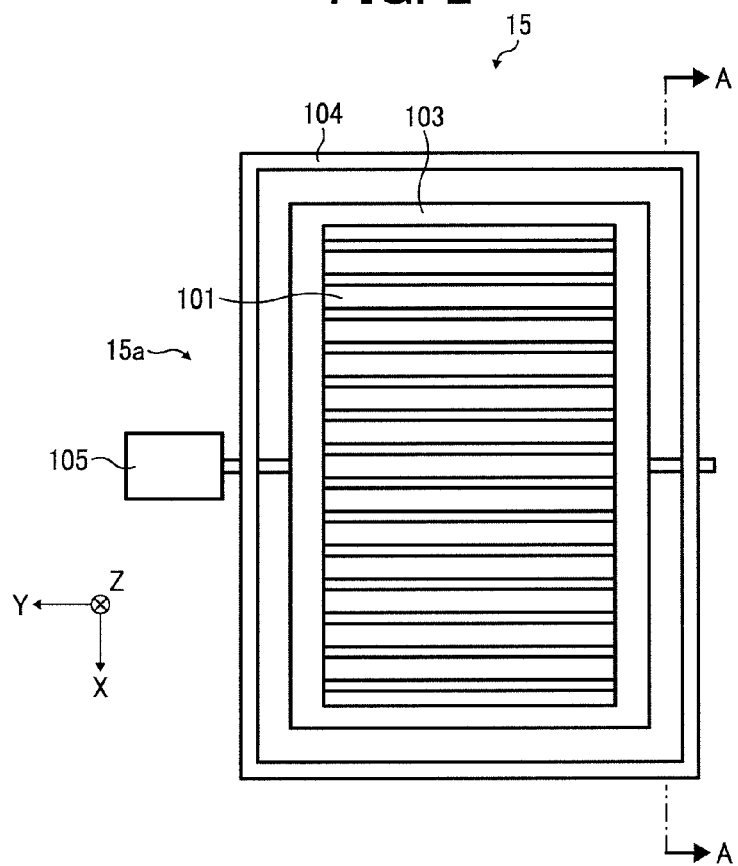
FIG. 2 is a view (Part 1) for explaining a filter unit shown in FIG. 1.
Figure 3:
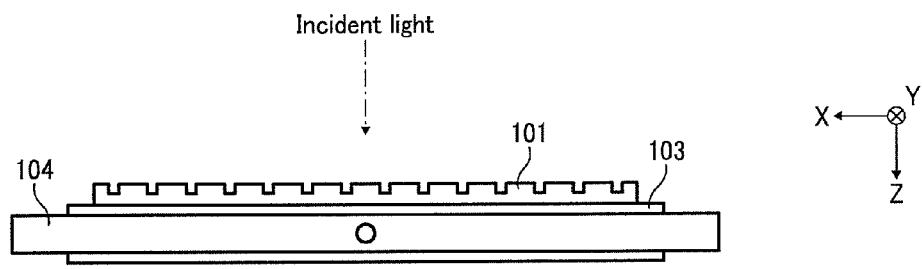
FIG. 3 is a view (Part 2) for explaining the filter unit shown in FIG. 1.
Figure 4:
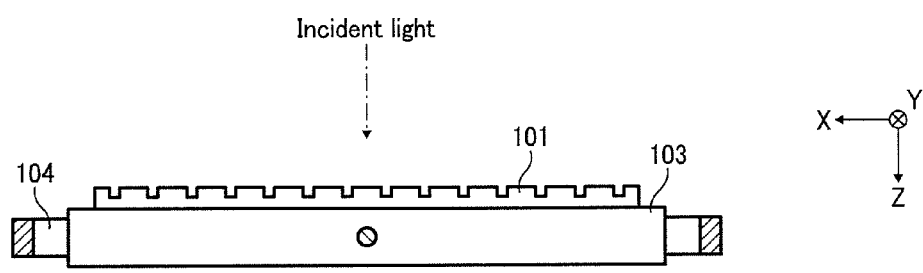
FIG. 4 is a cross sectional view taken along the line A-A of FIG. 2.

As shown by way of example in FIGS. 2 to 4, the optical filter unit 15 includes the wavelength selection filter 101 and a rotating mechanism 15a rotating the wavelength selection filter about an axis parallel to a surface of the substrate and perpendicular to the one axial direction. The rotating mechanism 15a includes a retaining member 103, a rotating support member 104, a driving mechanism 105, and the like. A light beam reflected by the wavelength selection filter 101 is outputted from the light source device 10. Incidentally, FIG. 4 is a cross sectional view taken along the A-A line of FIG. 2.

The wavelength selection filter 101 may be configured to selectively resonate and reflect light of a given wavelength contained in incident light. The wavelength selection filter 101 may include a substrate 101a having a rectangular waveform concave and convex structure which is formed on a plane on which the incident light falls incident. The concave and convex structure includes convex portions and concave portions which are arranged in one axial direction in a rectangular waveform in one axial direction, such as an axis of X, and a multilayer structure 101b such as a transparent film including a first layer 101b1 and a second layer 101b2 respectively coating one and the other one of side surfaces, in the one axial direction X, of each of convex portions of the concave and convex structure. A refractive index of the first layer 101b1 and a refractive index of the second layer 101b2 may be both higher than a refractive index of the substrate 101a. The refractive index of the first layer 101b1 may be equal to the refractive index of the second layer 101b2.

Figure 5:
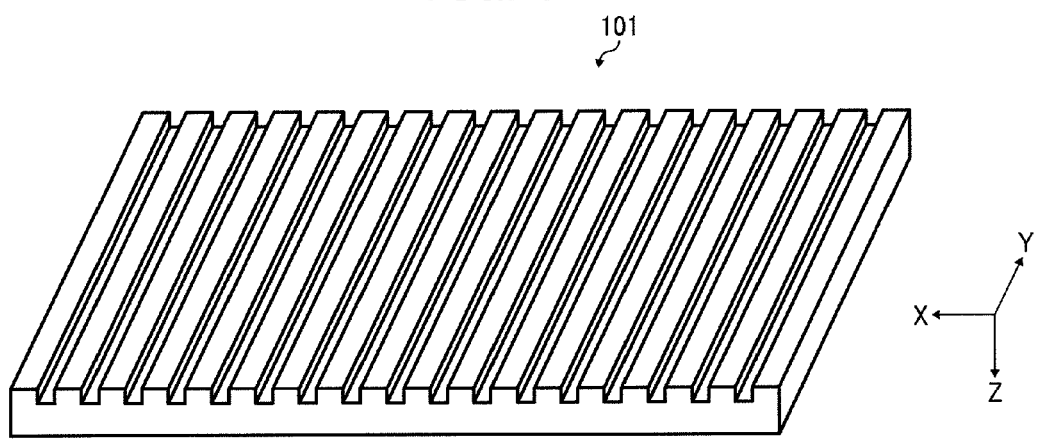
FIG. 5 is a view for explaining a wavelength selection filter 101 shown in FIG. 2.

As shown by way of example in FIG. 5, the wavelength selection filter 101 is a member in the form of plate, and has multiple straight-line grooves formed at regular intervals in a surface, on which the substantially collimated light bundle passed through the coupling lens 13 is incident, of the filter 101 (here, in the surface in a negative Z (−Z) direction). The X-axis direction is here shown as a direction where the grooves are arranged at the intervals, that is, a direction parallel to the direction of arrangement of the grooves.

Incidentally, in this embodiment, the wavelength selection filter 101 is designed, as an example, to perform selective reflection (or resonant reflection) of light with a wavelength of 605 nm when light of TM polarization falls incident on the wavelength selection filter 101 at an incident angle of 0°. In other words, the wavelength selection filter 101 is designed to have a resonant wavelength of 605 nm. Incidentally, the TM polarization refers to light whose magnetic field direction is parallel to the grooves. (See "*Kaisetsu Kogaku-soshi Nyumon* (Introduction to diffractive optics)," Optronics Co., Ltd., page 67.)

Figure 6:
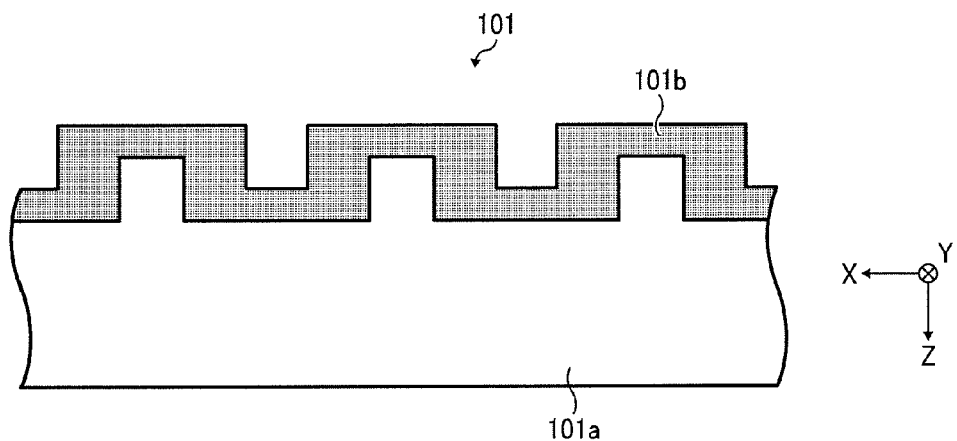
FIG. 6 is a view showing in enlarged dimension a portion of FIG. 5.

The wavelength selection filter 101 has the transparent substrate 101a and a transparent film 101b, as depicted in FIG. 6 showing in enlarged dimension a portion of FIG. 5.

Figure 10:
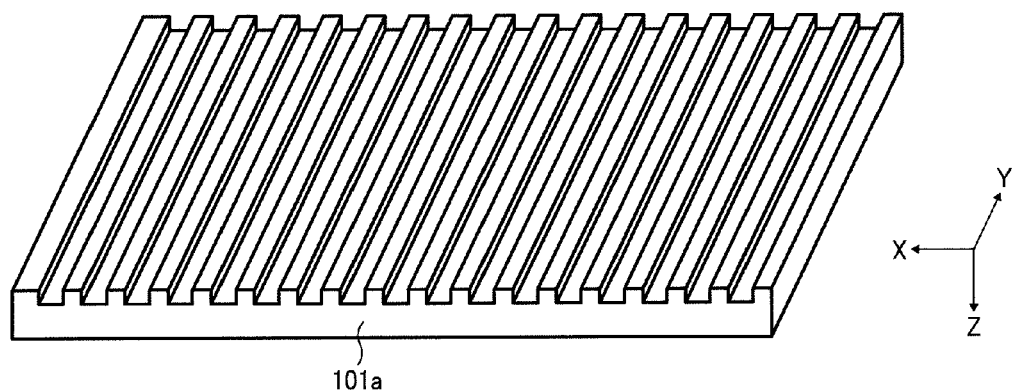
FIG. 10 is a perspective view of FIG. 8C.

The substrate 101a has a concave and convex structure in a rectangular waveform in the X-axis direction, in a surface in the negative Z direction (see FIG. 10). The concave and convex structure is coated with the transparent film 101b.

Quartz ($SiO_2$) with a refractive index of 1.46 is used, as an example, as a material for the substrate 101a. Also, tantalum pentoxide ($Ta_2O_5$) with a refractive index of 2.12 is used, as an example, as a material for the transparent film 101b.

The multilayer structure 101b may include a third layer 101b3 located between the first layer 101b1 and the second layer 101b2 in the one axial direction and a refractive index of the third layer 101b3 is lower than the refractive index of the substrate 101a. The third layer 101b3 may be an air layer. A width of each convex portion of the concave and convex structure, a width of the first layer 101b1, a width of the second layer 101b2, and a width of the third layer 101b3 may be equal to one another. A height of each convex portion of the concave and convex structure may be twice the width of the convex portion in the one axial direction.

Figure 7:
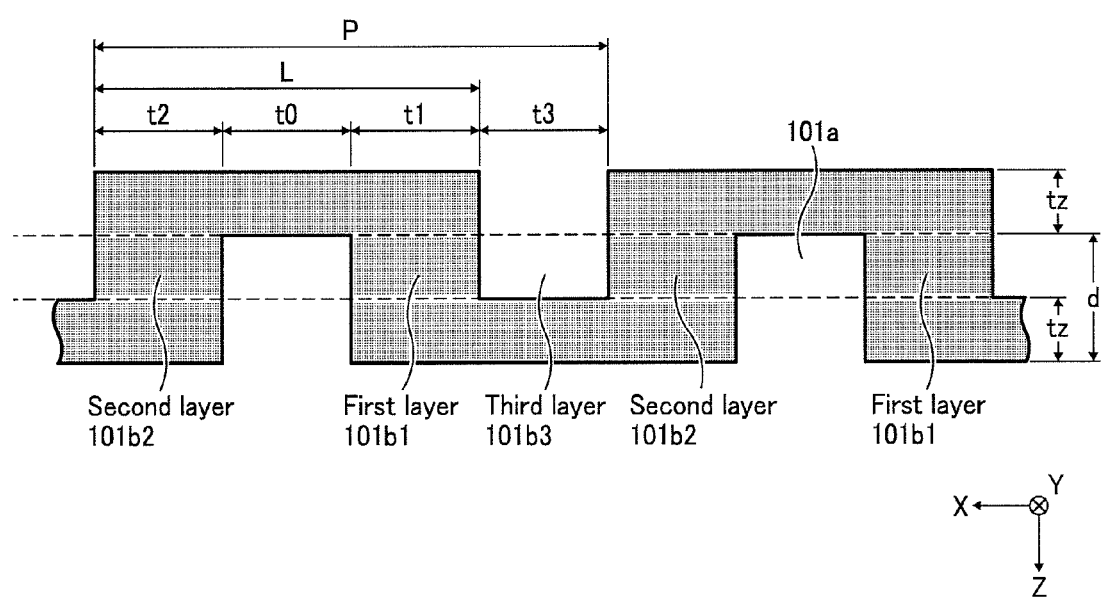
FIG. 7 is a view for explaining layers of the wavelength selection filter 101.

As shown in FIG. 7, first to third layers 101b3 are provided in the concave and convex structure of the substrate 101a. The first layer 101b1 is a part of the transparent film 101b adjacent to a convex portion of the concave and convex structure (hereinafter also called merely "convex portion" for the sake of convenience) on the negative X side. The second layer 101b2 is a part of the transparent film 101b adjacent to the convex portion on the positive X side. The third layer 101b3 is an air layer located between the first layer 101b1 and the second layer 101b2. Then, in the X-axis direction, the width of the convex portion is t0, the width of the first layer 101b1 is t1, the width of the second layer 101b2 is t2, and the width of the third layer 101b3 is t3. Also, the refractive index of the substrate 101a is n0, the refractive index of the first layer 101b1 is n1, the refractive index of the second layer 101b2 is n2, and the refractive index of the third layer 101b3 is n3. Further, the depth of the groove in the concave and convex structure of the substrate 101a is d.

Here, the width t0 is set to 100 nm, the width t1 is set to 100 nm, the width t2 is set to 100 nm, the width t3 is set to 100 nm, and the depth d is set to 100 nm. A pitch P is set to 400 nm, a land width L is set to 300 nm, and a filtering factor FF is set to 0.75 (=L/P).

The refractive index n0 is set to 1.46, the refractive index n1 is set to 2.12, the refractive index n2 is set to 2.12, and the refractive index n3 is set to 1.00. In other words, the relationship n1=n2>n0>n3 is satisfied.

Also, a film thickness tz of the transparent film 101b coating the top surface of the convex portion and the bottom surface of the concave portion is set to 50 nm.

Brief description will now be given of a method for manufacturing the wavelength selection filter 101.

Figure 8A:
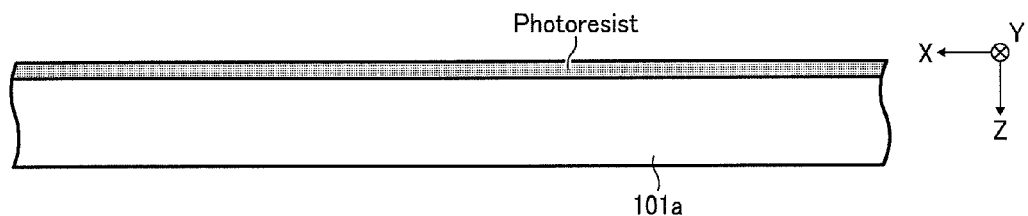
FIGS. 8A to 8D are views for explaining a method for manufacturing the wavelength selection filter.
Figure 8B:
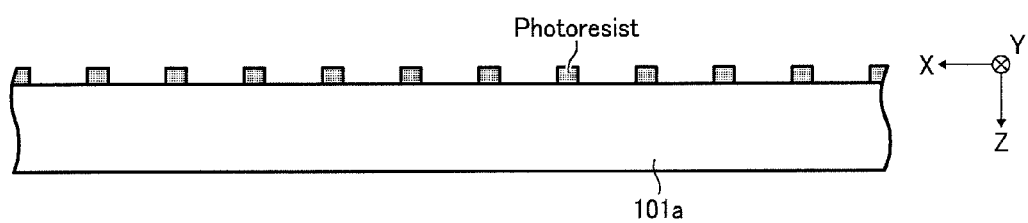
Figure 8C:
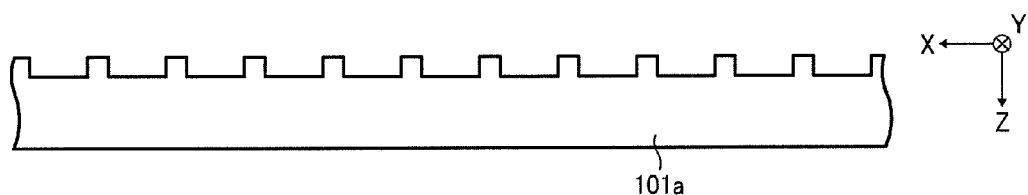

(1) A photoresist layer is formed by applying a photoresist on a surface (here, on the negative Z side) of the substrate 101a in the form of a flat plate (see FIG. 8A.).

(2) A predetermined lattice pattern is projected on the photoresist layer thereby to develop an image. Thus, a resist pattern in a lattice form is formed on the surface of the substrate 101a (see FIGS. 8B and 9).

(3) The substrate 101a having the resist pattern formed thereon is loaded in a dry etching apparatus such as an ion beam etching apparatus, a reactive ion etching apparatus, or a plasma etching apparatus, and is subjected to etching with the resist pattern used as a mask.

(4) The substrate 101a is unloaded from the dry etching apparatus when etched to a desired depth. Thereafter, the resist pattern is removed by elution using an organic solvent such as acetone, or by decomposition in oxygen plasma (see FIGS. 8C and 10). Thereby, the concave and convex structure in the rectangular waveform in the X-axis direction is formed in the surface of the substrate 101a.

Figure 8D:
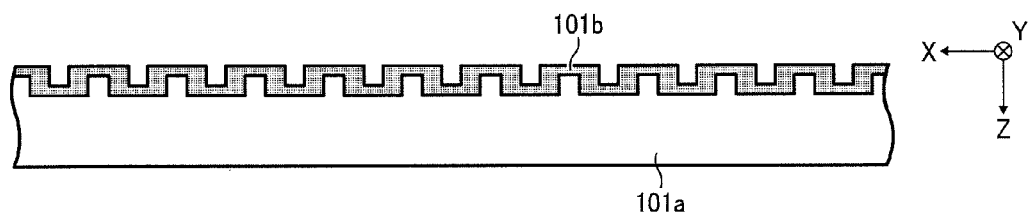
Figure 9:
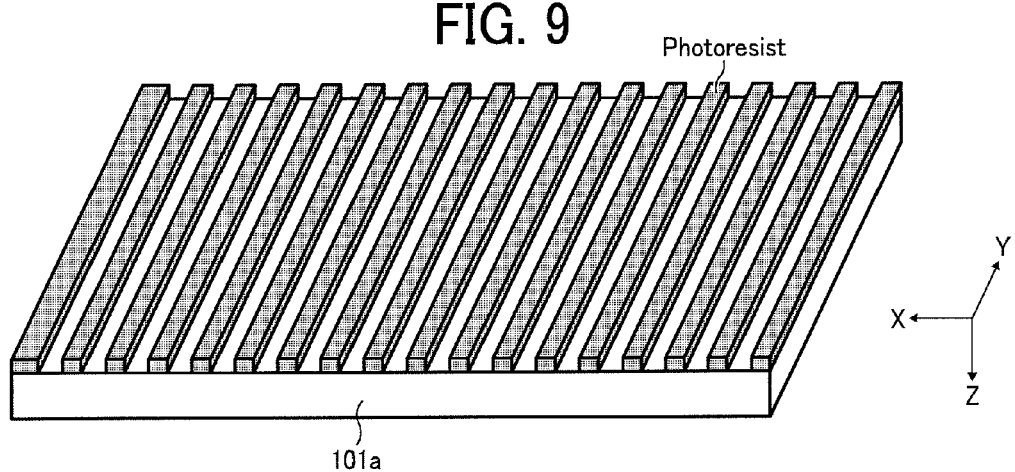
FIG. 9 is a perspective view of FIG. 8B.

(5) The transparent film 101b is formed on the concave and convex structure, using a physical vapor deposition (PVD) method, a chemical vapor deposition (CVD) method, or the like (see FIG. 8D). Incidentally, the transparent film 101b may be formed by applying a liquid material to the top of the concave and convex structure using spin coating, dipping or the like, and then, performing post-treatment such as a baking process. However, it is preferable to employ isotropic deposition means by which the transparent film 101b is formed also on the side of the convex portion.

Figure 11:
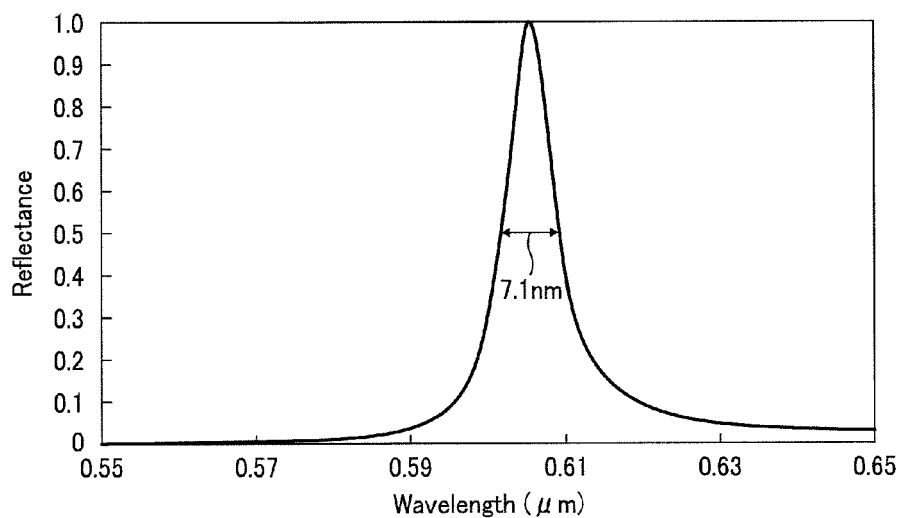
FIG. 11 is a graph for explaining the relationship between the wavelength and reflectance of incident light, which is observed in the wavelength selection filter.

FIG. 11 shows the relationship between the wavelength and reflectance of incident light of TM polarization, which is observed when the incident light falls incident at an incident angle of 0° on the wavelength selection filter 101 manufactured in the manner as described above. A wavelength (hereinafter, also called "peak wavelength") at which the highest reflectance is observed is 605 nm. A half-width of a peak waveform is 7.1 nm, which is extremely as narrow as about 1.2% of the peak wavelength. Also, at a wavelength at some distance from the peak wavelength, the reflectance is 0.1 or less. These results show the fact that the wavelength selection filter 101 functions as a wavelength selection filter for a narrow band centered at 605 nm, and that the reflectance of what is called unresonated reflected light is low. In other words, the wavelength selection filter 101 is suitable for reflection of only light lying within a desired wavelength range.

Figure 12:
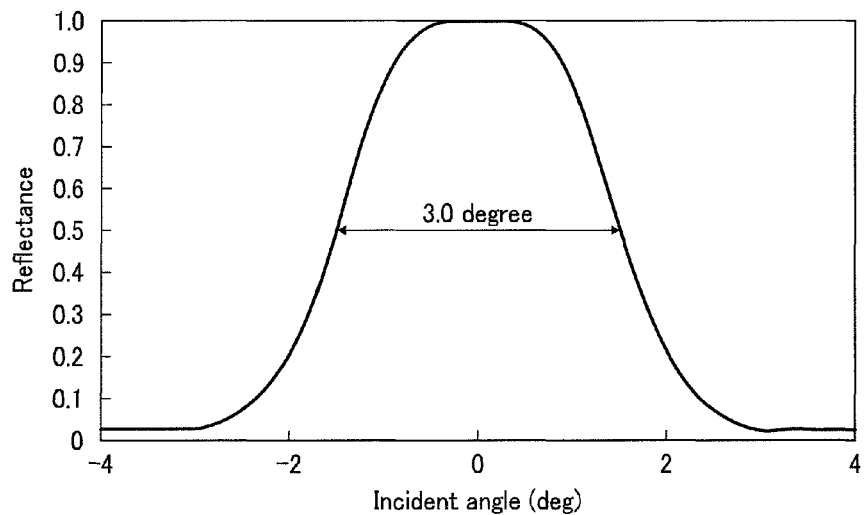
FIG. 12 is a graph for explaining the relationship between the incident angle and reflectance of incident light, which is observed in the wavelength selection filter.

FIG. 12 shows the relationship between the incident angle and reflectance of incident light, which is observed when the incident light with a wavelength of 605 nm falls incident on the wavelength selection filter 101. The half-width of the peak waveform is 3.0°.

Figure 13:
FIG. 13 is a view for explaining a wavelength selection filter of a comparative example.
Figure 14:
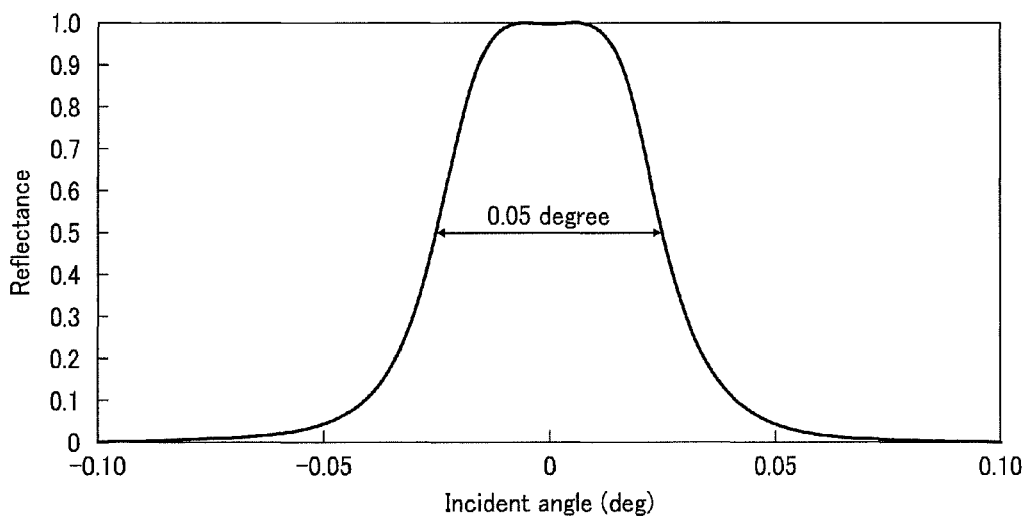
FIG. 14 is a graph for explaining the relationship between the incident angle and reflectance of incident light, which is observed in the wavelength selection filter of the comparative example.

For comparison, FIG. 14 shows the relationship between the incident angle and reflectance of incident light, which is observed when the incident light with a wavelength of 623.4 nm, which is a given wavelength, falls incident on the conventional wavelength selection filter (see FIG. 5(a) of Japanese Patent No. 3711446) in which the substrate has a concave and convex structure in the form of triangular waves as shown in FIG. 13. In this instance, the half-width of the peak waveform is 0.05°.

In other words, the allowable range of the incident angle for the wavelength selection filter 101 is about 60 times wider than that for the conventional wavelength selection filter. Incidentally, FIG. 14 shows the results of calculation using what is called RCWA (rigorous coupling wave analysis) method, assuming that the wavelength selection filter having the same structure as the wavelength filter disclosed in FIG. 5(a) of Japanese Patent No. 3711446 is used.

Accordingly, a large amount of reflected light can be obtained even if incident light is a somewhat diverging or converging light bundle. This allows for the relative positions of the light source 11 and the coupling lens 13 in the light source device 10, thus simplifying an assembly process and an adjustment process therefor. Also, an inexpensive lens can be used as the coupling lens 13. In other words, cost reduction of the light source device 10 can be achieved.

Figure 15A:
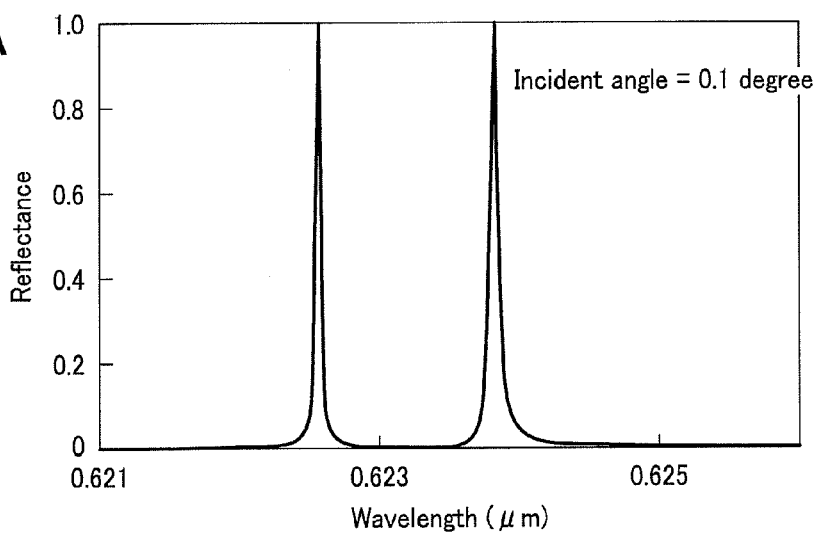
FIGS. 15A and 15B are graphs for explaining the relationship between the wavelength and reflectance of incident light when the incident angle is deviated from 0°, which is observed in the wavelength selection filter of the comparative example.
Figure 15B:
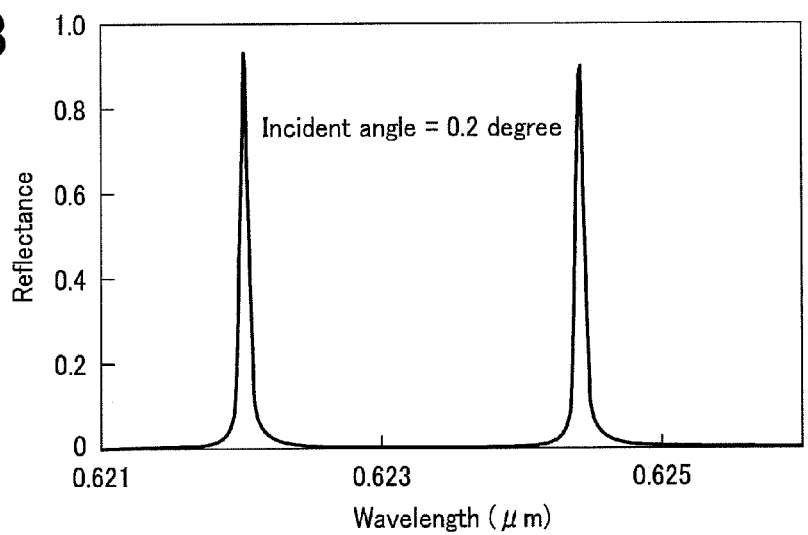
Figure 16:
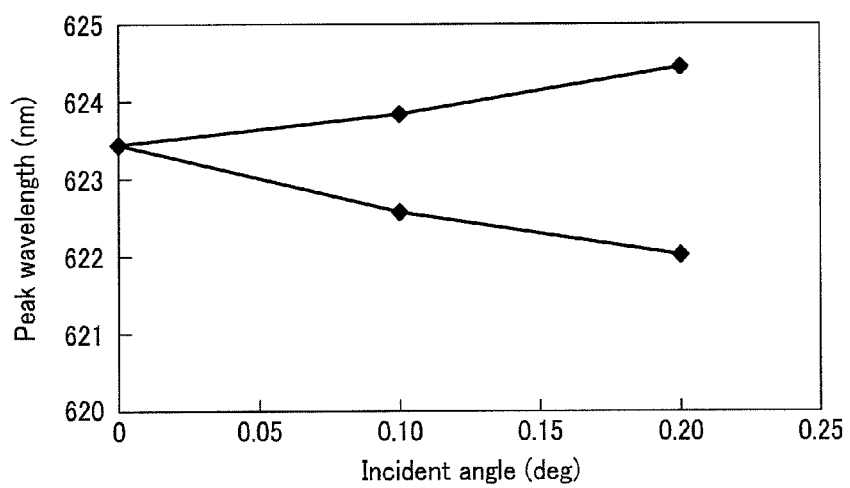
FIG. 16 is a graph for explaining the relationship between the incident angle and the peak wavelength of reflected light, which is observed in the wavelength selection filter of the comparative example.

Meanwhile, according to calculation, in the conventional wavelength selection filter (see FIG. 5(a) of Japanese Patent No. 3711446), deviation of the incident angle of incident light from 0° leads to two peaks appearing in terms of the relationship between the wavelength and reflectance of the incident light (see FIGS. 15A and 15B). FIG. 15A shows an instance where the incident angle is 0.1°, and FIG. 15B shows an instance where the incident angle is 0.2°. In both instances, each peak wavelength is different from the given wavelength, 623.4 nm. In other words, light of multiple wavelengths different from the given wavelength is reflected. When the deviation of the incident angle is small, the wavelength regions of the two peaks are so close that it is difficult to separate one of the wavelength regions from the other (see FIG. 16).

On the other hand, with the wavelength selection filter 101, only one peak appears in terms of the relationship between the wavelength and reflectance of incident light, even if the incident angle of the incident light deviates from 0°.

Figure 17A:
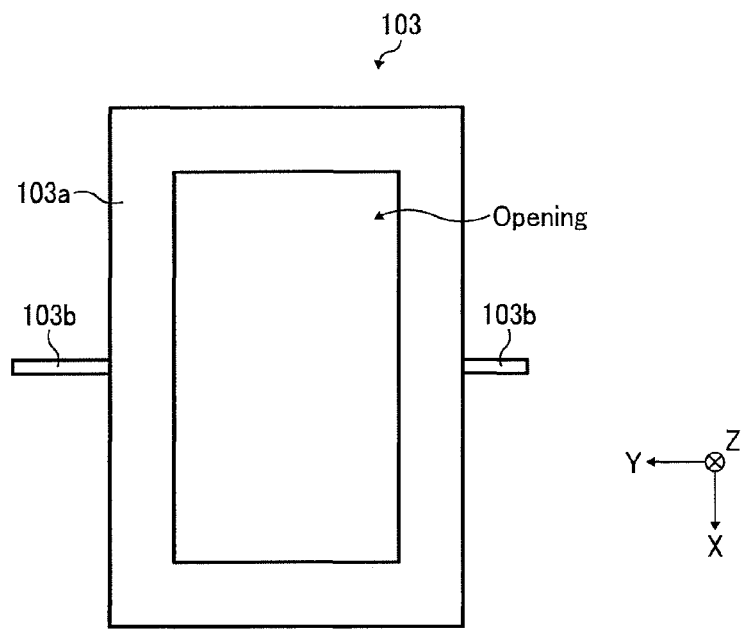
FIGS. 17A to 17C are views for explaining a retaining member shown in FIG. 2.
Figure 17B:
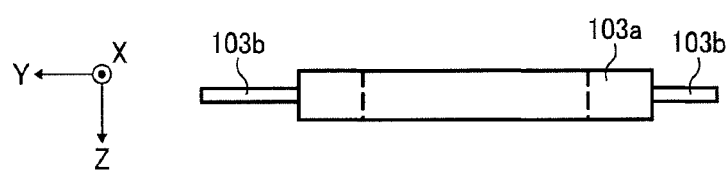
Figure 17C:
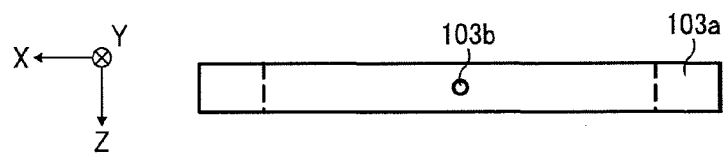
Figure 18:
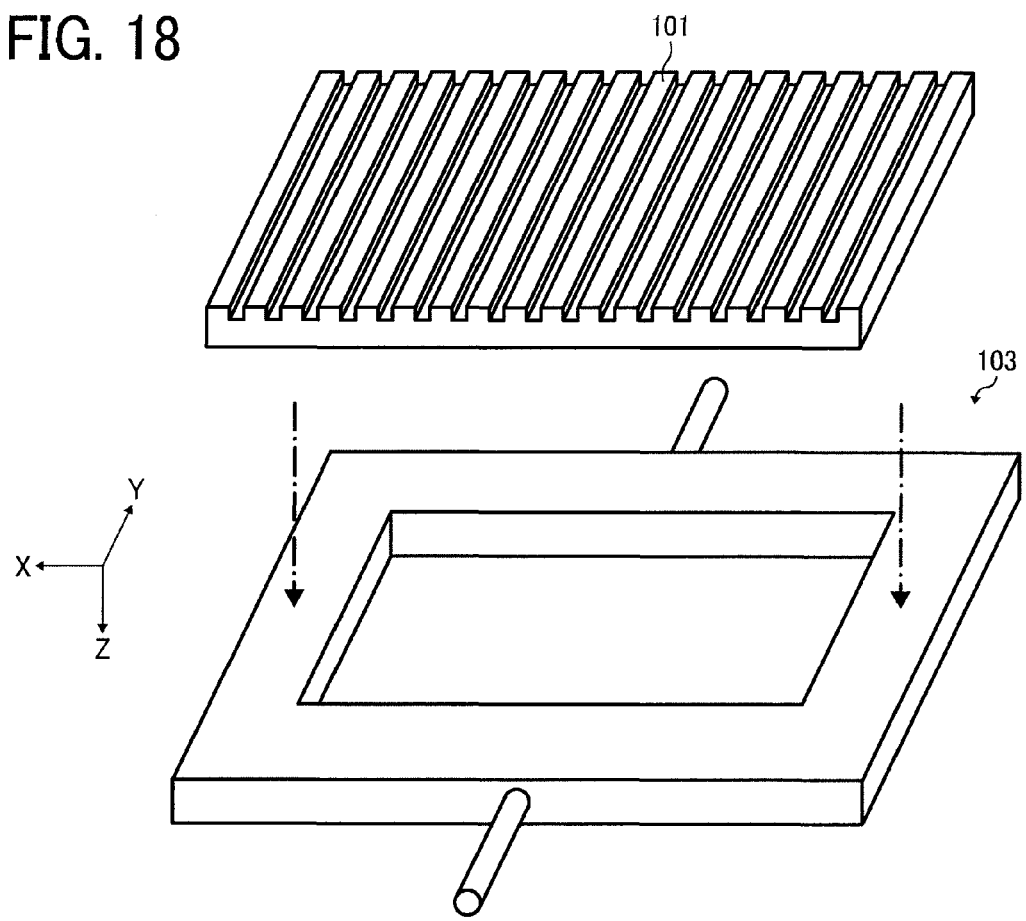
FIG. 18 is a view for explaining bonding between the wavelength selection filter and the retaining member.

The retaining member 103 is the member that retains the wavelength selection filter 101, and has a frame portion 103a having an opening at the center, and a projecting portion 103b in the form of a circular rod extending in the Y-axis direction, as shown by way of example in FIGS. 17A to 17C. The projecting portion 103b is provided at the center of a side surface of the frame portion 103a on the positive Y side and at the center thereof on the negative Y side. As shown in FIG. 18 for example, the retaining member 103 and the wavelength selection filter 101 is bonded together with a surface of the frame portion 103a on the negative Z side and a surface of the wavelength selection filter 101 on the positive Z side in between.

Figure 19A:
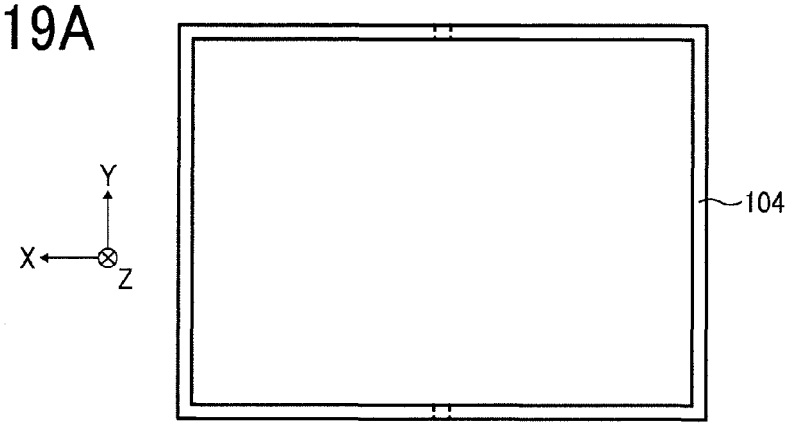
FIGS. 19A and 19B are views for explaining a rotating support member shown in FIG. 2.
Figure 19B:
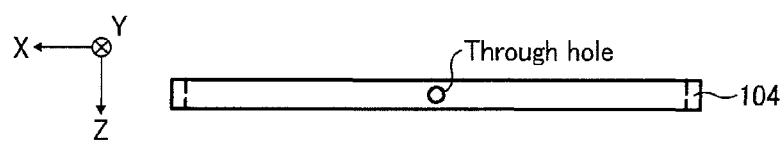

The rotating support member 104 is the member that supports the retaining member 103, and has an opening larger than the frame portion 103a of the retaining member 103 at the center, as shown by way of example in FIGS. 19A and 19B for example. Also, the rotating support member 104 has through holes for supporting the projecting portions 103b of the retaining member 103.

Figure 20:
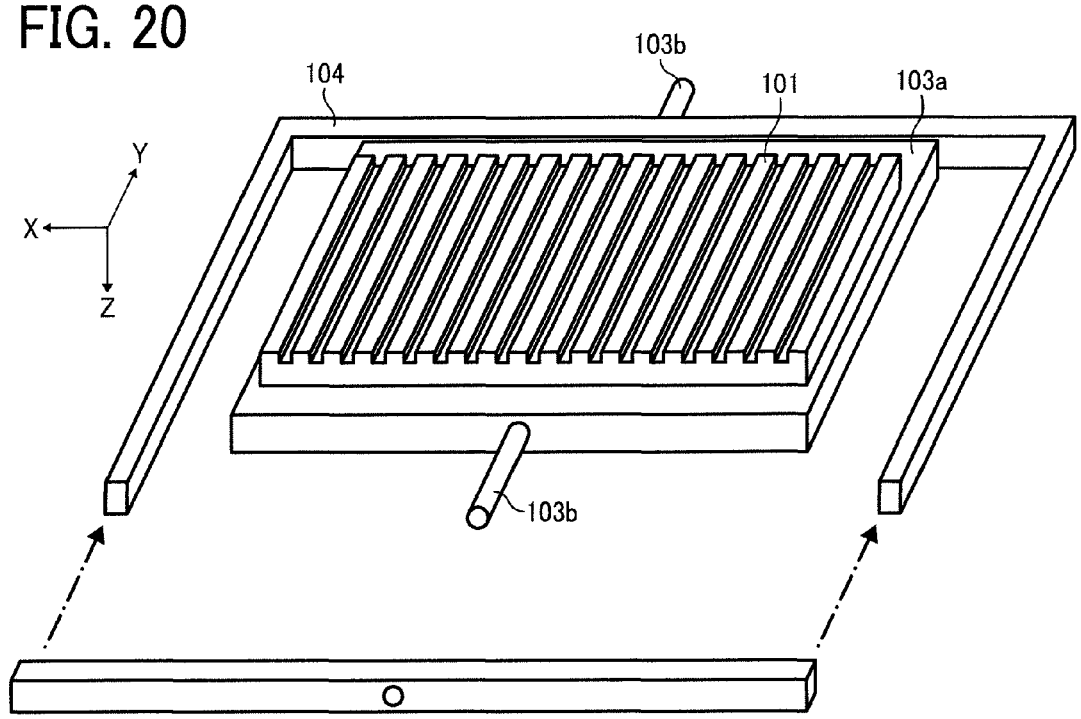
FIG. 20 is a view (Part 1) for explaining the support of the retaining member by the rotating support member.
Figure 21:
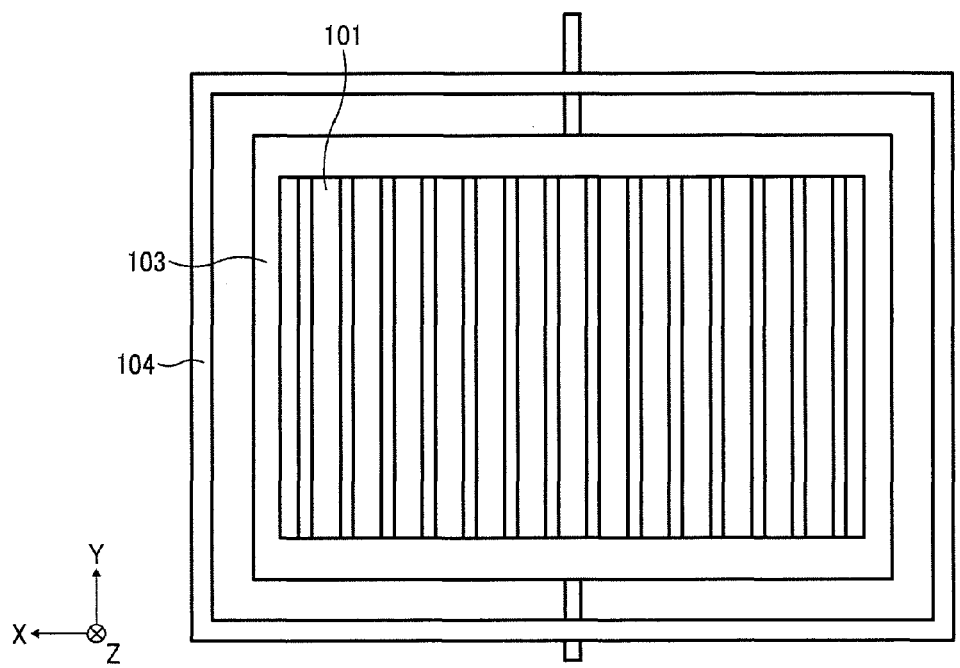
FIG. 21 is a view (Part 2) for explaining the support of the retaining member by the rotating support member.

As shown by way of example in FIG. 20, at least a portion of the rotating support member 104, which has the through hole, is removable so that the projecting portions 103b of the retaining member 103 can be easily inserted into the through holes (see FIG. 21).

Figure 22A:
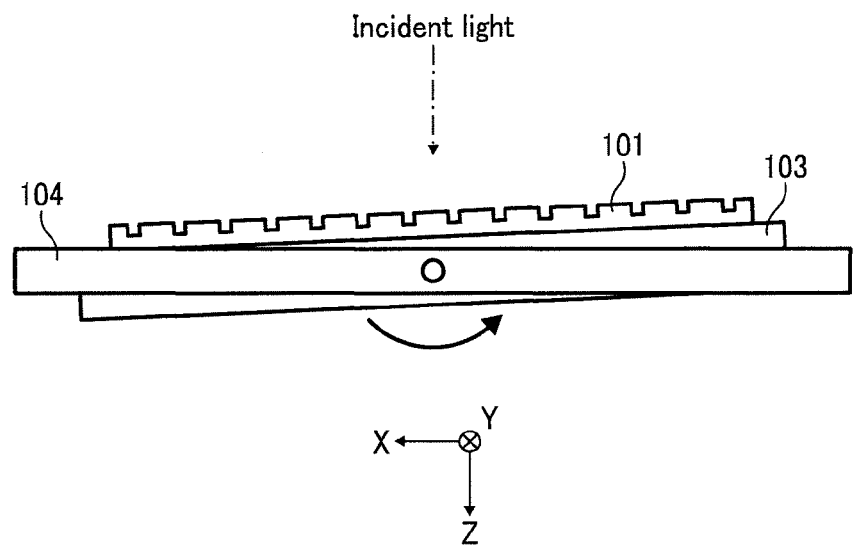
FIGS. 22A and 22B are views for explaining rotation of the retaining member.
Figure 22B:
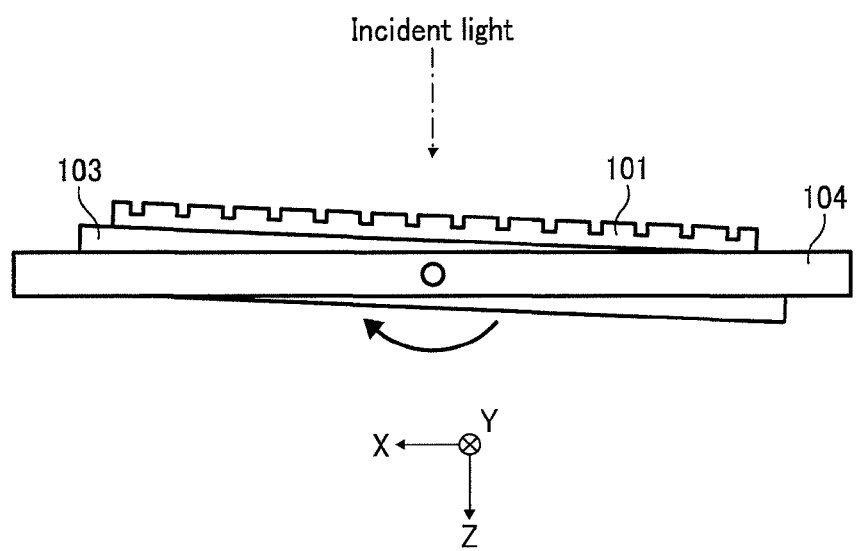

The driving mechanism 105 rotates one of the projecting portions 103b of the retaining member 103, and thereby inclines the retaining member 103 with respect to the rotating support member 104, as shown by way of example in FIGS. 22A and 22B. As a result, the incident angle of incident light with respect to the wavelength selection filter 101 can be changed.

Figure 23:
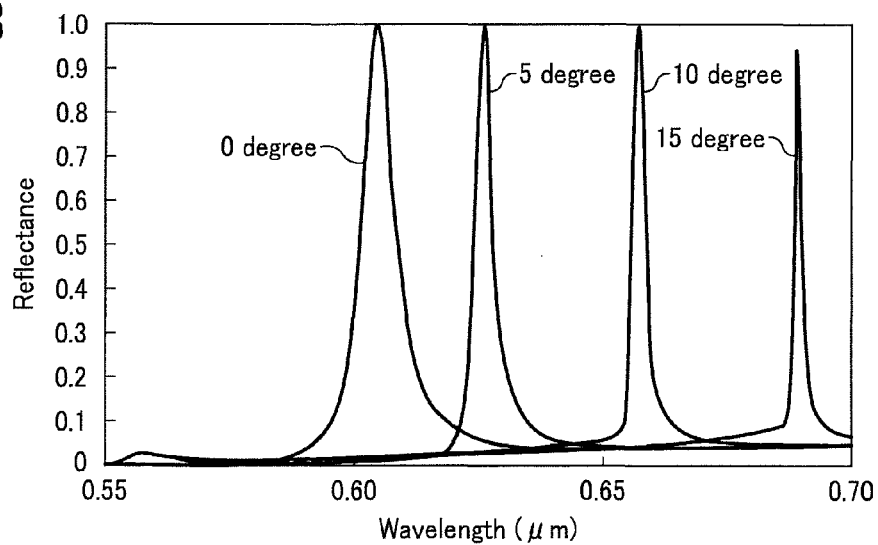
FIG. 23 is a graph for explaining the relationship between the wavelength and reflectance of incident light at different incident angles, which is observed in the wavelength selection filter.
Figure 24:
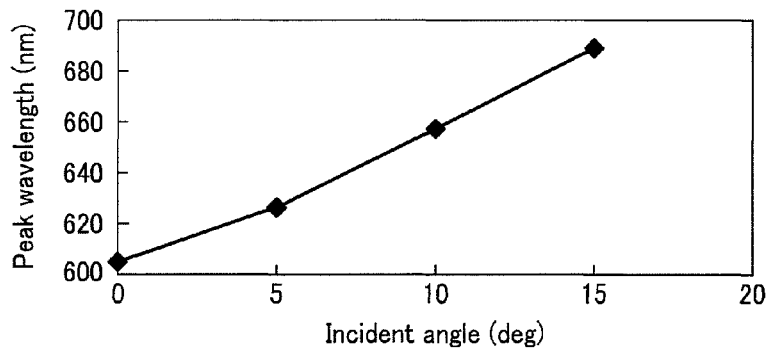
FIG. 24 is a graph for explaining the relationship between the incident angle and the peak wavelength of reflected light, which is observed in the wavelength selection filter.

FIG. 23 shows the relationship between the wavelength and reflectance of incident light in the wavelength selection filter 101 at different incident angles (0°, 5°, 10°, and 15°). Also, FIG. 24 shows the relationship between the incident angle of the incident light and the peak wavelength of reflected light in the wavelength selection filter 101. These results show the fact that greater incident angle leads to higher peak wavelength.

Thus, the driving mechanism 105 can be used to change the incident angle of incident light with respect to the wavelength selection filter 101, thereby to adjust the wavelength of light reflected by the wavelength selection filter 101. In other words, the wavelength region of the light beam outputted from the light source device 10 and a center wavelength of the wavelength region can be made variable. Incidentally, the driving mechanism 105 may be configured to rotate the projecting portions 103b by hand, or to rotate the projecting portions 103b electrically by using a motor, for example.

The driving mechanism 105 includes a lock mechanism (not shown) that locks the rotation position of the retaining member 103, and is configured to be able to lock the rotation position of the retaining member 103 when the wavelength of light reflected by the wavelength selection filter 101 is a desired wavelength.

Incidentally, the reflecting mirror 17 can adjust its attitude so that the direction where the light beam is outputted from the light source device 10 is the positive Z direction at all times.

Figure 25:
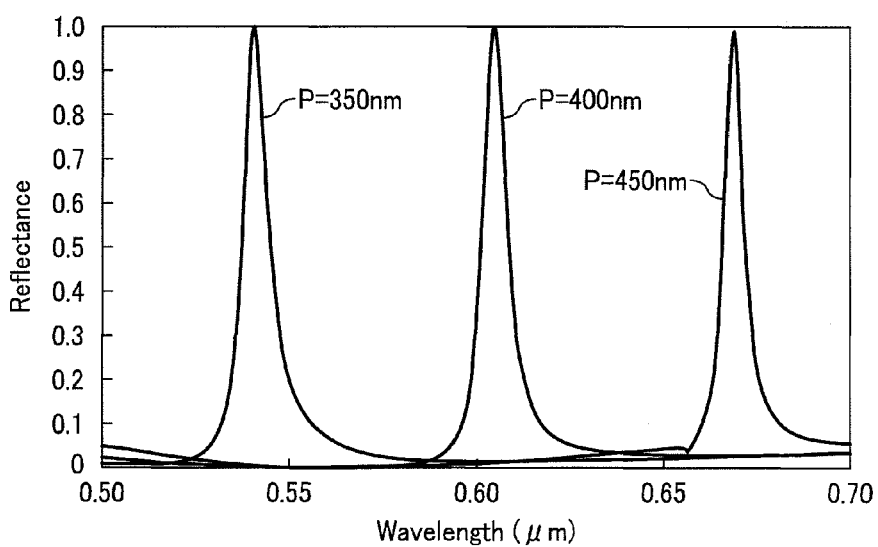
FIG. 25 is a graph for explaining the relationship between the wavelength and reflectance of incident light at different pitches, which is observed in the wavelength selection filter.
Figure 26:
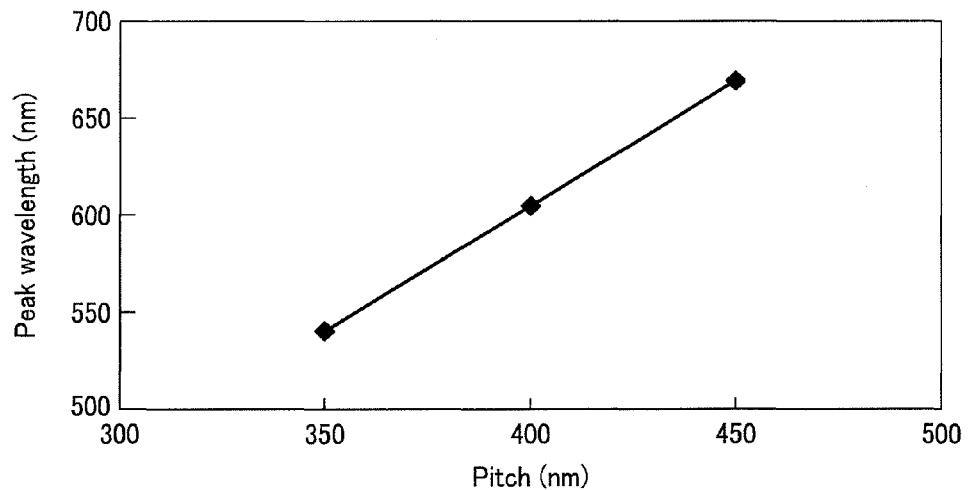
FIG. 26 is a graph for explaining the relationship between the pitch and the peak wavelength of reflected light, which is observed in the wavelength selection filter.

Incidentally, the wavelength selection filter 101 may change the peak wavelength of reflected light by changing the pitch P, as shown in FIGS. 25 and 26. This can be utilized to manufacture a wavelength selection filter having a reflection band according to the purpose, and having the same structure and characteristics as the wavelength selection filter 101. Incidentally, in FIGS. 25 and 26, the pitch P is changed while the relationship $t0=t1=t2=t3$ is maintained.

As described above, the wavelength selection filter 101 according to this embodiment includes the substrate 101a formed on the side on which incident light falls incident and having the concave and convex structure in the form of rectangular waves as viewed in the X-axis direction, and the transparent film 101b coating the concave and convex structure. In other words, both sides of each projecting portion of the concave and convex structure on the positive and negative X sides are coated with the transparent film 101b. The refractive index of the transparent film 101b is higher than that of the substrate 101a.

Also, the air layer is provided between the transparent film 101b at a part adjacent to one projecting portion on the positive X side and the transparent film 101b at a part adjacent to a different projecting portion on the negative X side, the different projecting portion being adjacent to the one projecting portion.

Accordingly, the wavelength selectivity can be enhanced and the allowable range of the incident angle of light can be widened as compared to the conventional filter.

Also, the optical filter unit 15 according to this embodiment has the wavelength selection filter 101 having the enhanced wavelength selectivity and the wide allowable range of the incident angle of light, and thus can easily reflect only light of a desired wavelength without a cost increase.

Also, the light source device 10 according to this embodiment includes the optical filter unit 15 capable of reflecting only light of a desired wavelength without a cost increase, and consequently can easily output light of a desired wavelength without a cost increase.

Incidentally, in the embodiment, titanium oxide ($TiO_2$) with a refractive index of 2.35, niobium pentoxide ($Nb_2O_5$) with a refractive index of 2.33, or aluminum oxide ($Al_2O_3$) with a refractive index of 1.63 may be used as the material for the transparent film 101b.

Also, in the embodiment, description has been given of the wavelength selection filter designed to have a resonant wavelength of 605 nm; however, the present invention is not limited thereto. A wavelength selection filter 201 designed to have a resonant wavelength of 623 nm is shown by way of example in FIG. 27.

As is the case with the wavelength selection filter 101, the wavelength selection filter 201 is a member in the form of plate, and has multiple straight-line grooves formed at regular intervals in a surface, on which light is incident, of the filter 201.

Figure 27:
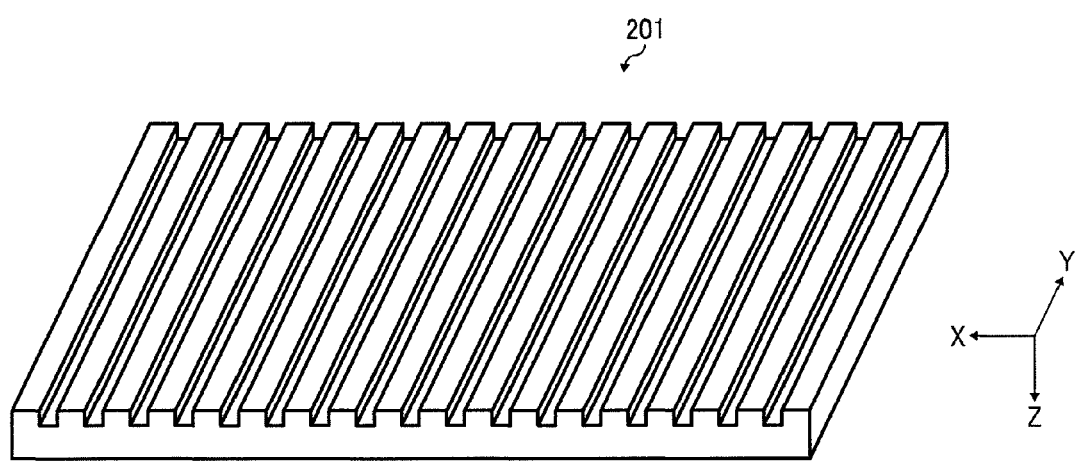
FIG. 27 is a view for explaining a wavelength selection filter.
Figure 28:
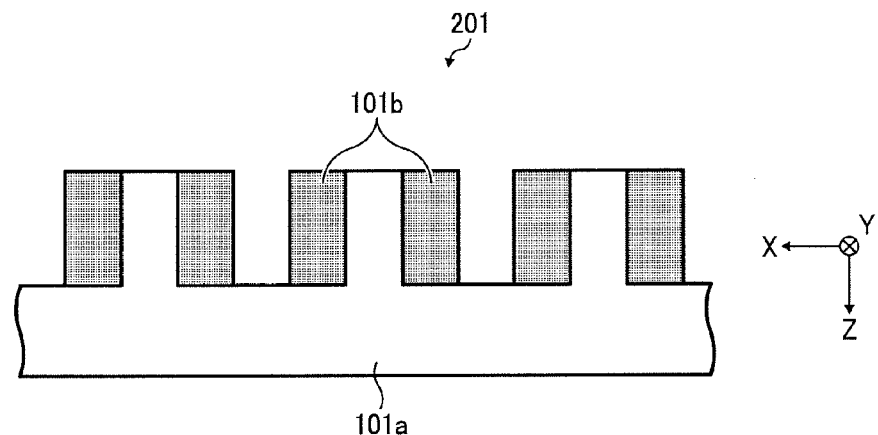
FIG. 28 is a view showing in enlarged dimension a portion of FIG. 27.

As depicted in FIG. 28 showing in enlarged dimension a portion of FIG. 27, the wavelength selection filter 201 has the substrate 101a having the concave and convex structure formed thereon, and the transparent film 101b. However, the transparent film 101b coats only the side surfaces of each convex portion, as distinct from the wavelength selection filter 101. In other words, in the concave and convex structure, both surfaces of each convex portion on the positive and negative X sides are coated with the transparent film 101b.

Figure 29:
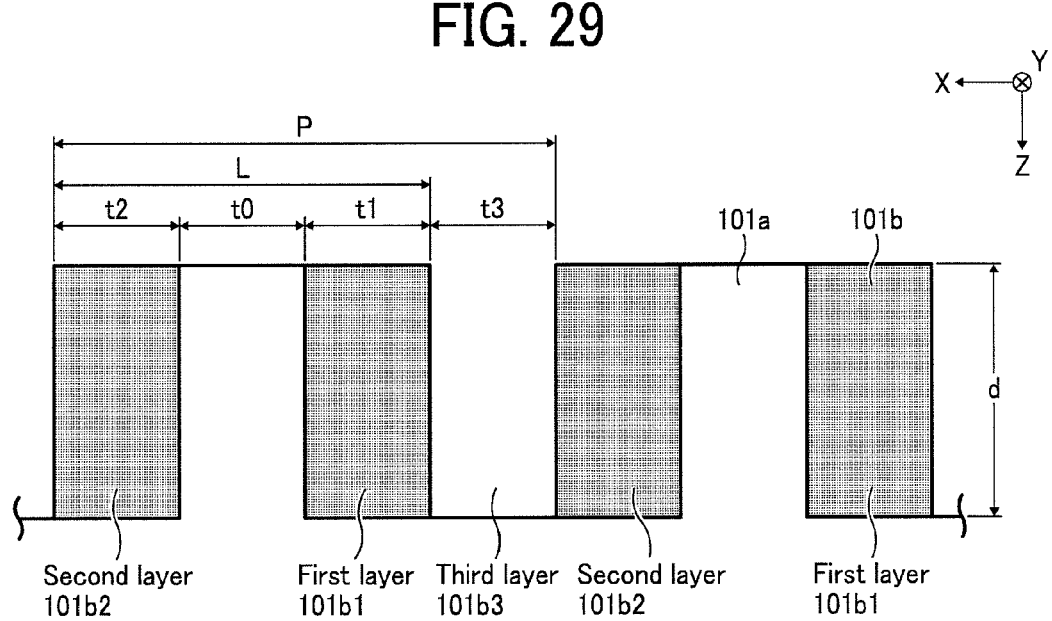
FIG. 29 is a view for explaining layers of the wavelength selection filter.

Here, the width t0 is set to 100 nm, the width t1 is set to 100 nm, the width t2 is set to 100 nm, the width t3 is set to 100 nm, and the depth d is set to 200 nm (see FIG. 29). The pitch P is set to 400 nm, the land width L is set to 300 nm, and the filtering factor FF is set to 0.75 (=L/P).

The refractive index n0 is set to 1.46, the refractive index n1 is set to 2.12, the refractive index n2 is set to 2.12, and the refractive index n3 is set to 1.00. In other words, the relationship n1=n2>n0>n3 is satisfied.

Brief description will be given of a method for manufacturing the wavelength selection filter 201.

Figure 30A:
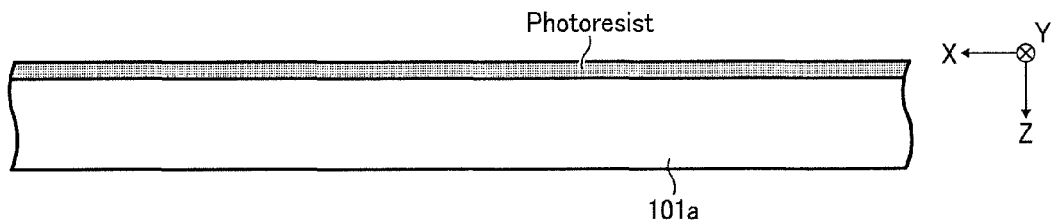
FIGS. 30A to 30E are views for explaining a method for manufacturing the wavelength selection filter.

(1) A photoresist layer is formed by applying a photoresist on a surface (here, on the negative Z side) of the substrate 101a in the form of a flat plate (see FIG. 30A).

Figure 30B:
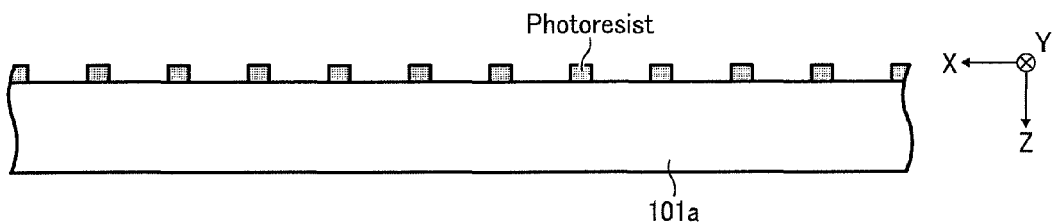

(2) A predetermined lattice pattern is projected on the photoresist layer thereby to develop an image. Thereby, a resist pattern in lattice form is formed on the surface of the substrate 101a (see FIG. 30B).

(3) The substrate 101a having the resist pattern formed thereon is loaded in the dry etching apparatus, and is subjected to etching with the resist pattern used as a mask.

Figure 30C:
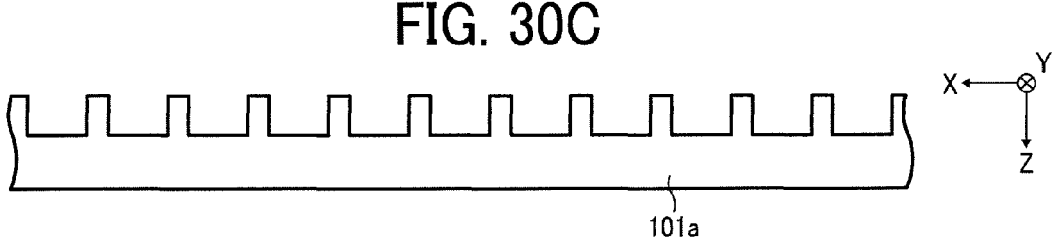

(4) The substrate 101a is unloaded from the dry etching apparatus when etched to a desired depth. Thereafter, the resist pattern is removed (see FIG. 30C). Thereby, the concave and convex structure in the rectangular waveform in the X-axis direction is formed in the surface of the substrate 101a.

Figure 30D:
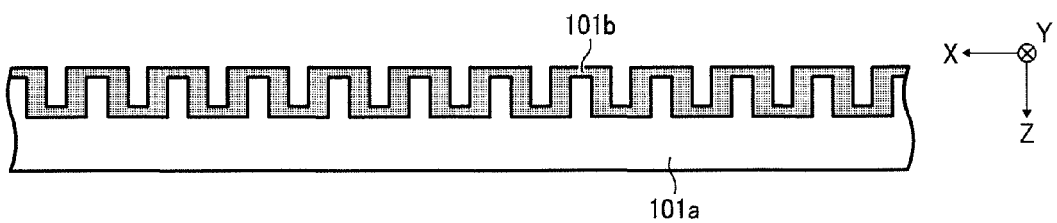

(5) The transparent film 101b is formed on the concave and convex structure, using a physical vapor deposition (PVD) method, a chemical vapor deposition (CVD) method, or the like (see FIG. 30D).

Figure 30E:
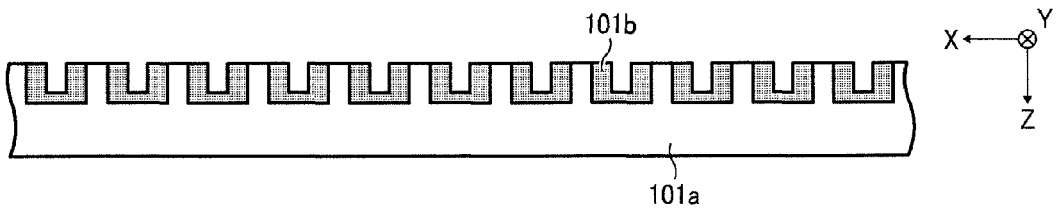

(6) The transparent film 101b formed on the top surface of the convex portions and the bottom surface of the concave portions is removed by dry-etching the substrate 101a having the transparent film 101b formed thereon (see FIG. 30E). Highly anisotropic dry etching is possible depending on conditions. Thus, by appropriately selecting a plasma condition and the like, it is possible to etch the substrate 101a in a vertical direction while suppressing etching of the transparent film 101b formed on the side surfaces of the concave portions and convex portions.

Figure 31:
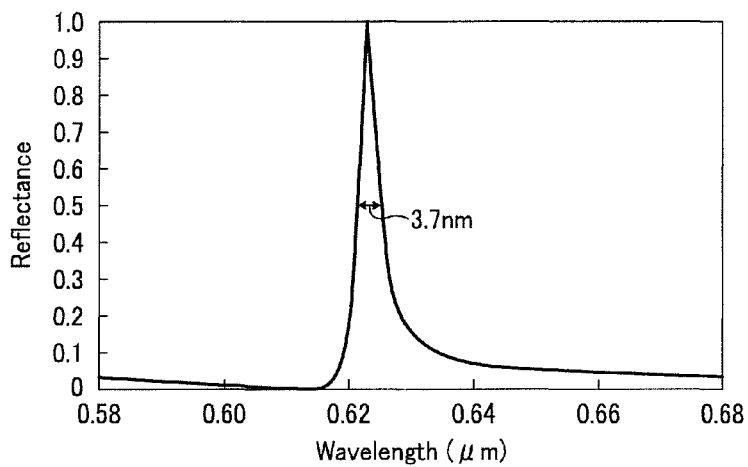
FIG. 31 is a graph for explaining the relationship between the wavelength and reflectance of incident light, which is observed in the wavelength selection filter.

FIG. 31 shows the relationship between the wavelength and reflectance of incident light of TM polarization, which is observed when the incident light falls incident at an incident angle of 0° on the wavelength selection filter 201 manufactured in the manner as described above. The peak wavelength is 623 nm. The half-width of the peak waveform is 3.7 nm, which is extremely as narrow as about 0.6% of the peak wavelength. Also, at a wavelength at some distance from the peak wavelength, the reflectance is 0.1 or less. These results show the fact that the wavelength selection filter 201 functions as a wavelength selection filter for a narrow band centered at 623 nm, and that the reflectance of what is called unresonated reflected light is low. In other words, the wavelength selection filter 201 is suitable for reflection of only light lying within a desired wavelength range.

Figure 32:
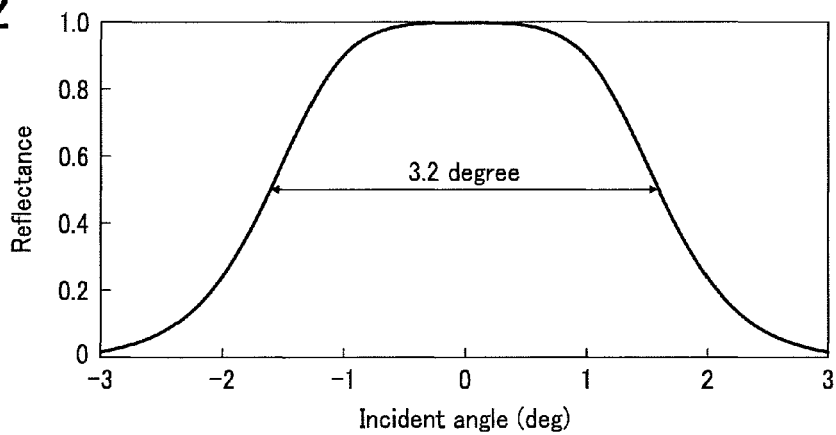
FIG. 32 is a graph for explaining the relationship between the incident angle and reflectance of incident light, which is observed in the wavelength selection filter.

FIG. 32 shows the relationship between the incident angle and reflectance of incident light, which is observed when the incident light with a wavelength of 623 nm falls incident on the wavelength selection filter 201. The half-width of the peak waveform is 3.2°. In other words, the allowable range of the incident angle for the wavelength selection filter 201 is about 64 times wider than that for the conventional wavelength selection filter.

Accordingly, a large amount of reflected light can be obtained even if incident light is a somewhat diverging or converging light bundle.

Moreover, with the wavelength selection filter 201, only one peak appears in terms of the relationship between the wavelength and reflectance of the incident light, even if the incident angle of the incident light deviates from 0°.

Figure 33:
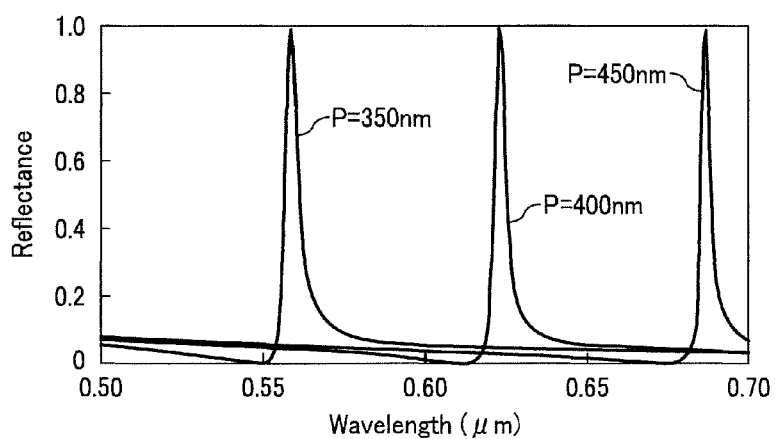
FIG. 33 is a graph for explaining the relationship between the wavelength and reflectance of incident light at different pitches, which is observed in the wavelength selection filter.
Figure 34:
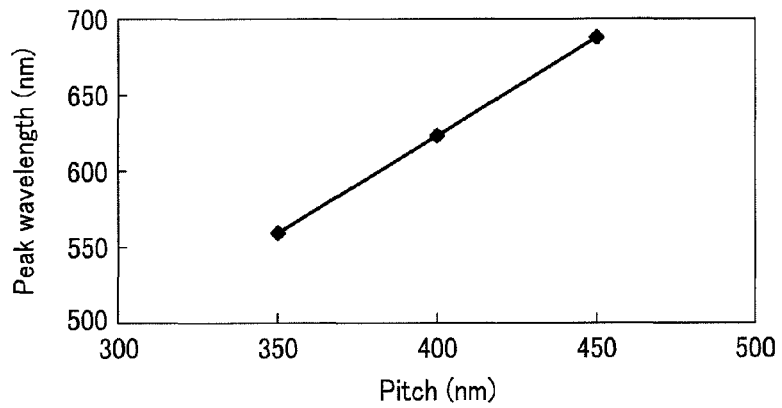
FIG. 34 is a graph for explaining the relationship between the pitch and the peak wavelength of reflected light, which is observed in the wavelength selection filter.

Further, the wavelength selection filter 201 may change the peak wavelength of reflected light by changing the pitch P, as shown in FIGS. 33 and 34. This can be utilized to manufacture a wavelength selection filter having a reflection band according to the purpose, and having the same structure and characteristics as the wavelength selection filter 201. Incidentally, in FIGS. 33 and 34, the pitch P is changed while the relationship t0=t1=t2=t3 is maintained.

Figure 35:
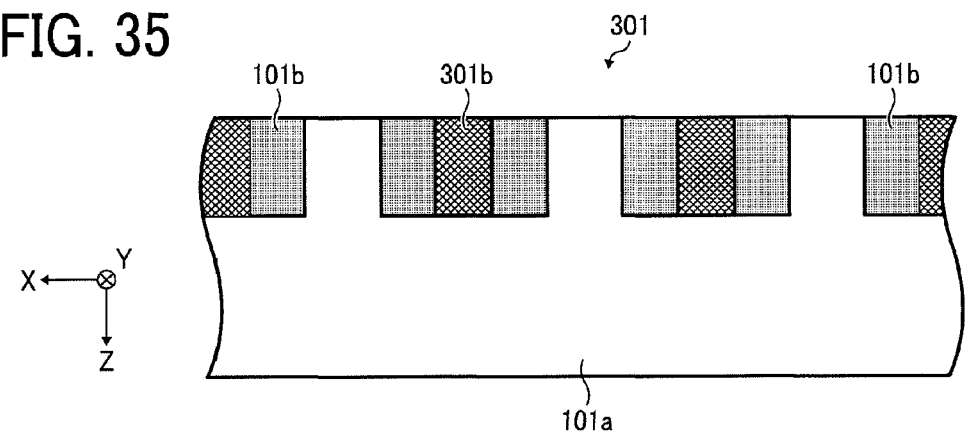
FIG. 35 is a view for explaining a wavelength selection filter.

A wavelength selection filter 301 designed to have a resonant wavelength of 630 nm is shown by way of example in FIG. 35.

As shown in FIG. 35, in the wavelength selection filter 301, the third layer 101b3 of the wavelength selection filter 201 is replaced with a transparent material 301b with a refractive index of 1.25.

Figure 36:
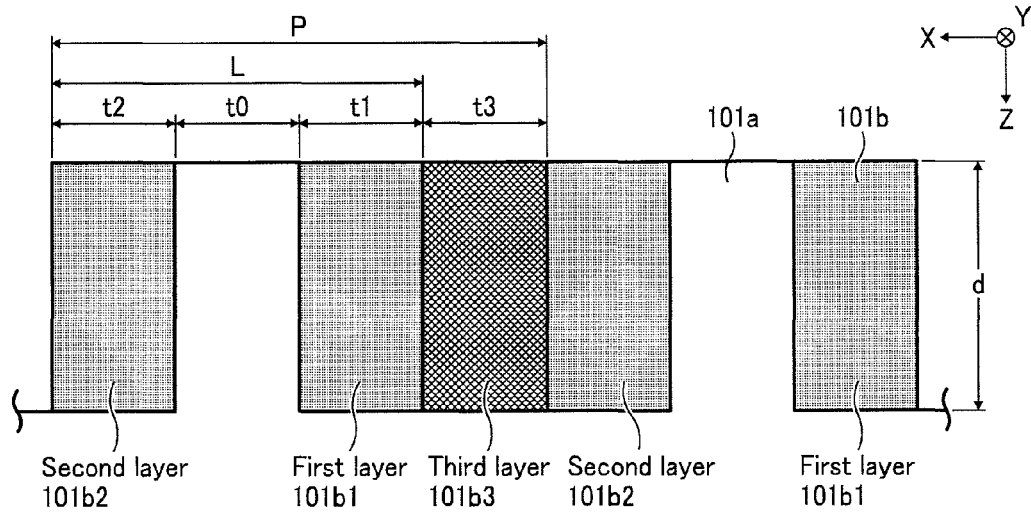
FIG. 36 is a view for explaining layers of the wavelength selection filter.

Here, the width t0 is set to 100 nm, the width t1 is set to 100 nm, the width t2 is set to 100 nm, the width t3 is set to 100 nm, and the depth d is set to 200 nm (see FIG. 36). The pitch P is set to 400 nm, the land width L is set to 300 nm, and the filtering factor FF is set to 0.75 (=L/P).

The refractive index n0 is set to 1.46, the refractive index n1 is set to 2.12, the refractive index n2 is set to 2.12, and the refractive index n3 is set to 1.25. In other words, the relationship n1=n2>n0>n3 is satisfied.

Brief description will be given of a method for manufacturing the wavelength selection filter 301.

Figure 37A:
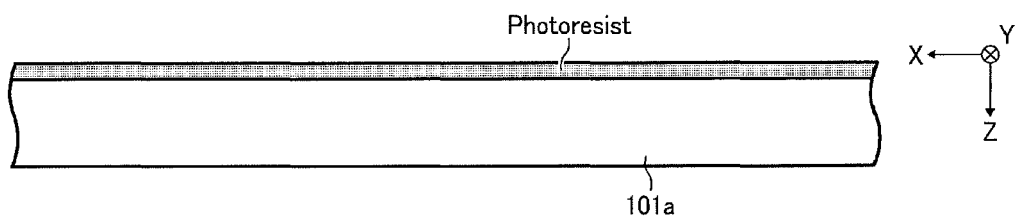
FIGS. 37A to 37D are views (Part 1) for explaining a method for manufacturing the wavelength selection filter.

(1) A photoresist layer is formed by applying a photoresist on a surface (here, on the negative Z side) of the substrate 101a in the form of a flat plate (see FIG. 37A).

Figure 37B:
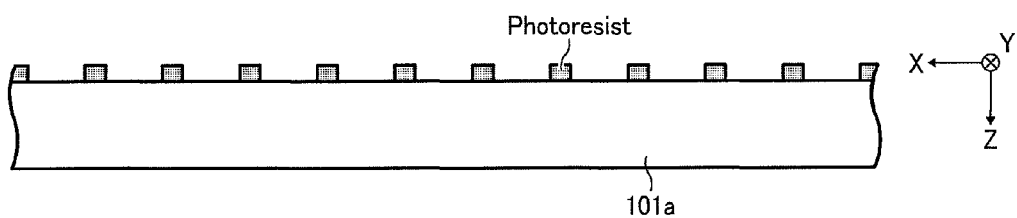

(2) A predetermined lattice pattern is projected on the photoresist layer thereby to develop an image. Thereby, a resist pattern in lattice form is formed on the surface of the substrate 101a (see FIG. 37B).

(3) The substrate 101a having the resist pattern formed thereon is loaded in the dry etching apparatus, and is subjected to etching with the resist pattern used as a mask.

Figure 37C:
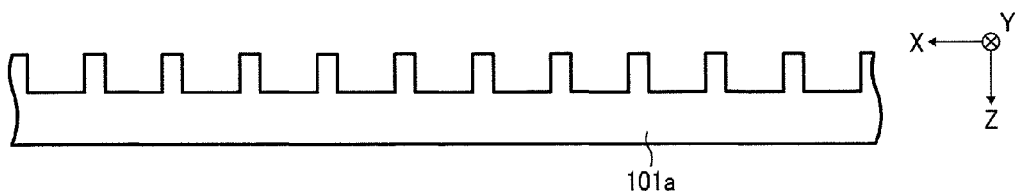

(4) The substrate 101a is unloaded from the dry etching apparatus when etched to a desired depth. Thereafter, the resist pattern is removed (see FIG. 37C). Thereby, the concave and convex structure in the rectangular waveform in the X-axis direction is formed in the surface of the substrate 101a.

Figure 37D:
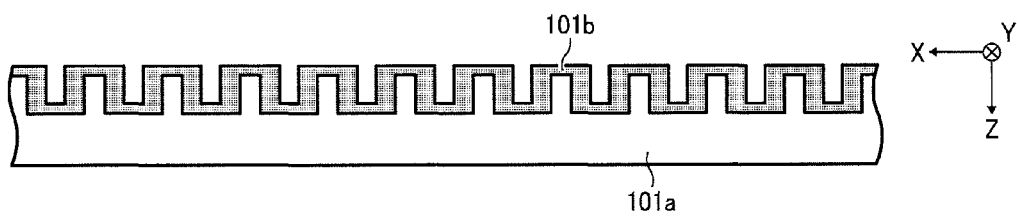

(5) The transparent film 101b is formed on the concave and convex structure, using a physical vapor deposition (PVD) method, a chemical vapor deposition (CVD) method, or the like (see FIG. 37D).

Figure 38A:
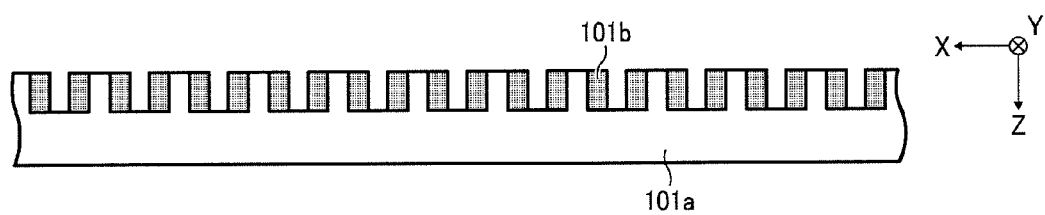
FIGS. 38A to 38C are views (Part 2) for explaining a method for manufacturing the wavelength selection filter.

(6) The transparent film 101b formed on the top surface of the convex portions and the bottom surface of the concave portions is removed by dry-etching the substrate 101a having the transparent film 101b formed thereon (see FIG. 38A).

Figure 38B:
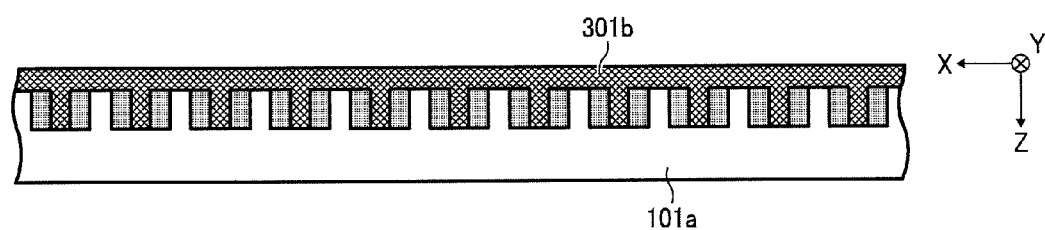

(7) A layer of the transparent material 301b is formed on the transparent film 101b thus etched, using a physical vapor deposition (PVD) method, a chemical vapor deposition (CVD) method, or the like (see FIG. 38B).

Figure 38C:
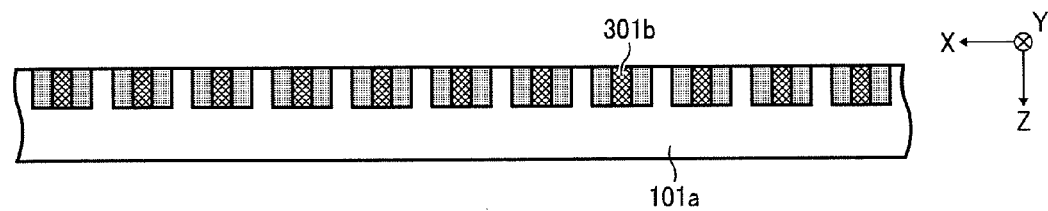

(8) The transparent material 301b which coats the top surfaces of the convex portions and the transparent film 101b is removed by dry etching (see FIG. 38C).

Figure 39:
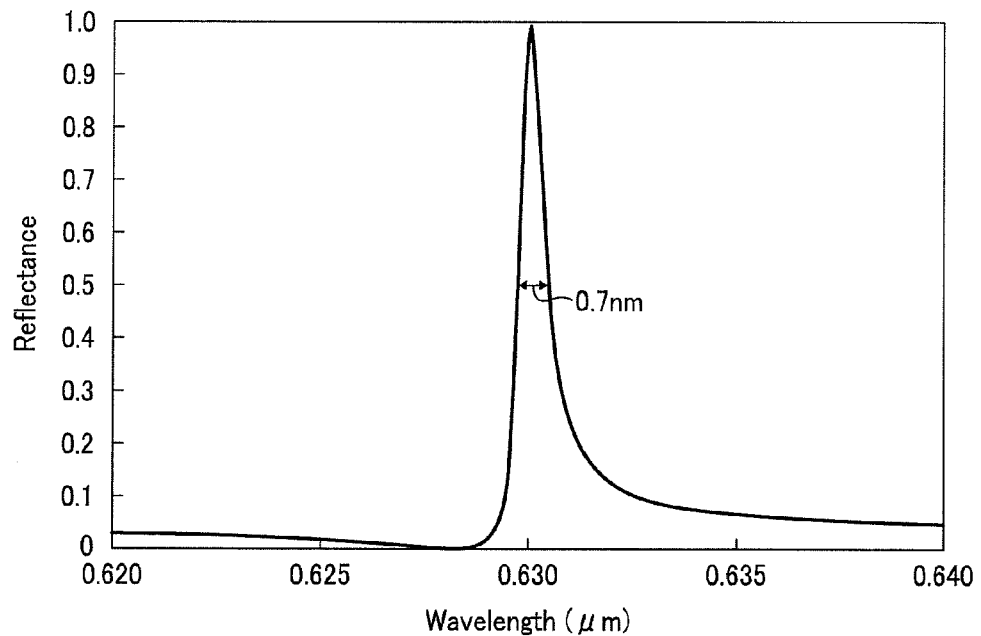
FIG. 39 is a graph for explaining the relationship between the wavelength and reflectance of incident light, which is observed in the wavelength selection filter.

FIG. 39 shows the relationship between the wavelength and reflectance of incident light of TM polarization, which is observed when the incident light falls incident at an incident angle of 0° on the wavelength selection filter 301 manufactured in the manner as described above. The peak wavelength is 630 nm. The half-width of the peak waveform is 0.7 nm, which is extremely as narrow as about 0.1% of the peak wavelength. Also, at a wavelength at some distance from the peak wavelength, the reflectance is 0.1 or less. These results show the fact that the wavelength selection filter 301 functions as a wavelength selection filter for a narrow band centered at 630 nm, and that the reflectance of what is called unresonated reflected light is low. In other words, the wavelength selection filter 301 is suitable for reflection of only light lying within a desired wavelength range.

Figure 40:
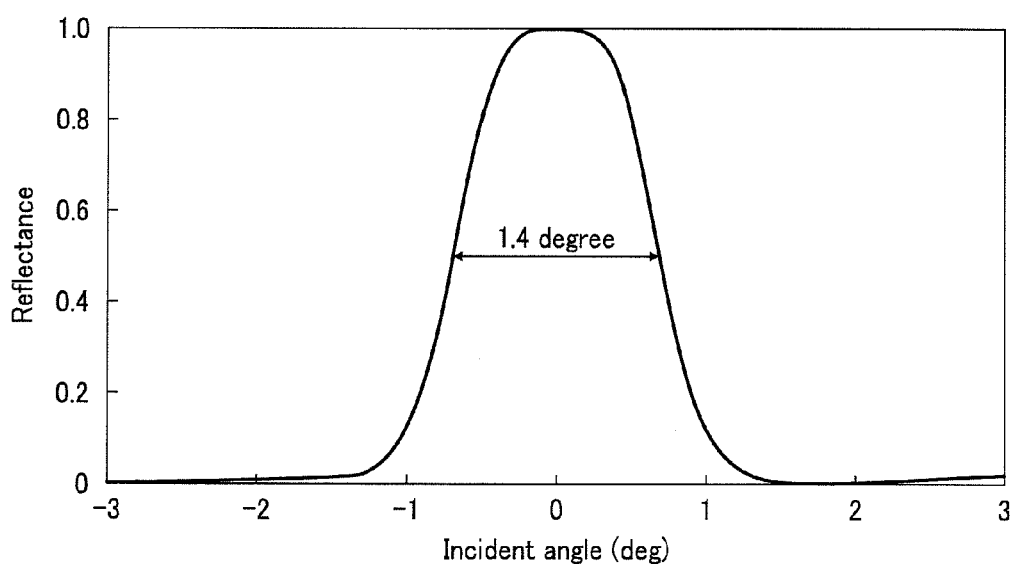
FIG. 40 is a graph for explaining the relationship between the incident angle and reflectance of incident light, which is observed in the wavelength selection filter.

FIG. 40 shows the relationship between the incident angle and reflectance of incident light, which is observed when the incident light with a wavelength of 630 nm falls incident on the wavelength selection filter 301. The half-width of the peak waveform is 1.4°. In other words, the allowable range of the incident angle for the wavelength selection filter 301 is about 28 times wider than that for the conventional wavelength selection filter.

Accordingly, a large amount of reflected light can be obtained even if incident light is a somewhat diverging or converging light bundle.

Moreover, with the wavelength selection filter 301, only one peak appears in terms of the relationship between the wavelength and reflectance of the incident light, even if the incident angle of the incident light deviates from 0°.

Figure 41:
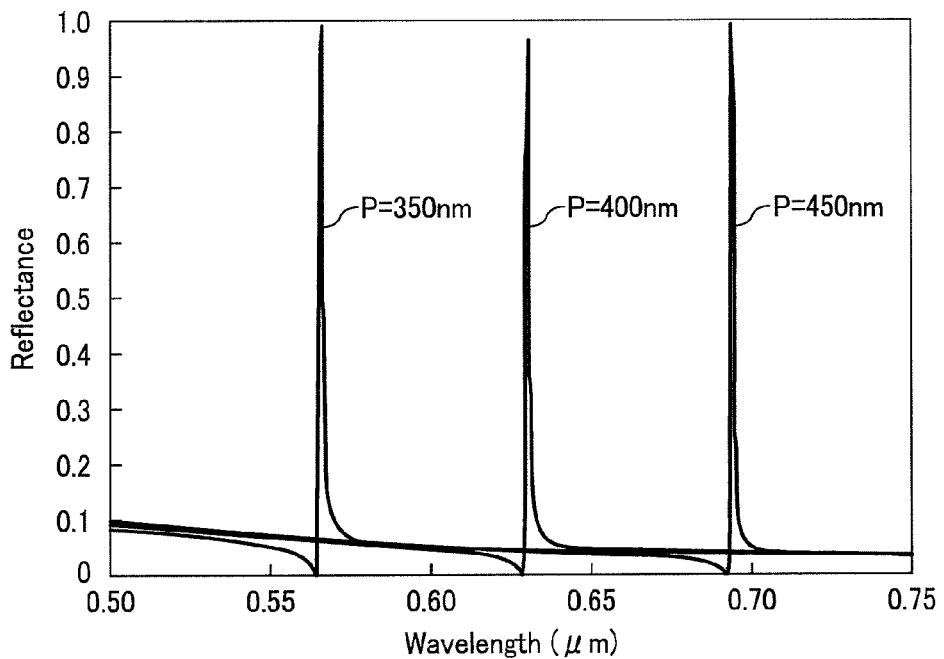
FIG. 41 is a graph for explaining the relationship between the wavelength and reflectance of incident light at different pitches, which is observed in the wavelength selection filter.
Figure 42:
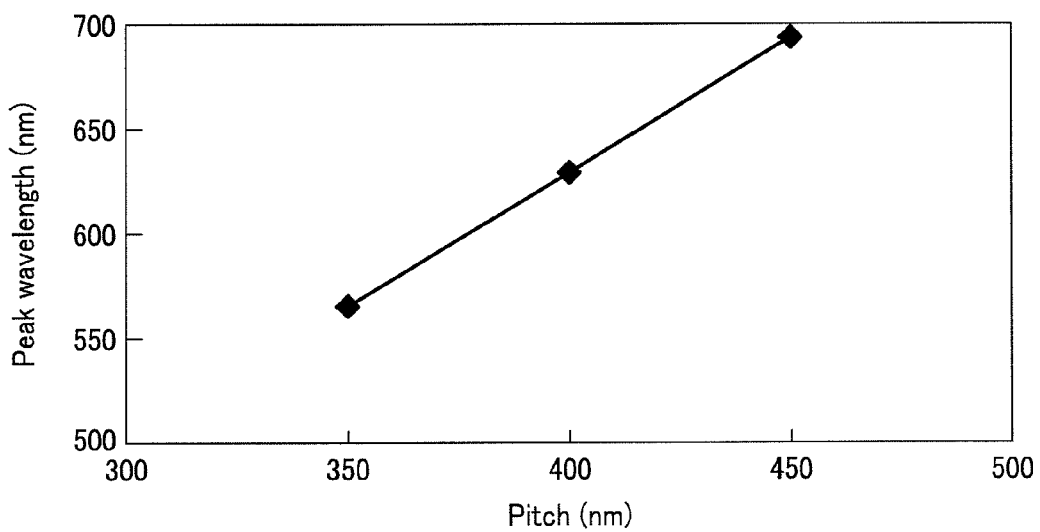
FIG. 42 is a graph for explaining the relationship between the pitch and the peak wavelength of reflected light, which is observed in the wavelength selection filter.

Further, the wavelength selection filter 301 may change the peak wavelength of reflected light by changing the pitch P, as shown in FIGS. 41 and 42. This can be utilized to manufacture a wavelength selection filter having a reflection band according to the purpose, and having the same structure and characteristics as the wavelength selection filter 301.

Figure 43:
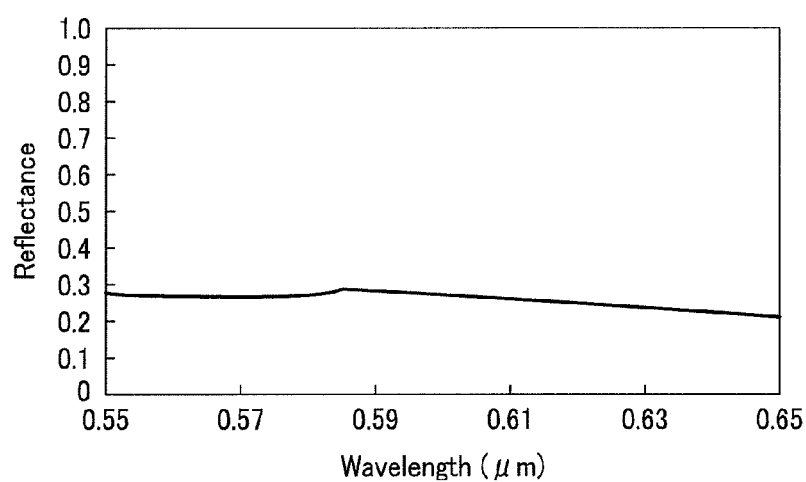
FIG. 43 is a graph for explaining a comparative example 1 of the wavelength selection filter.
Figure 44:
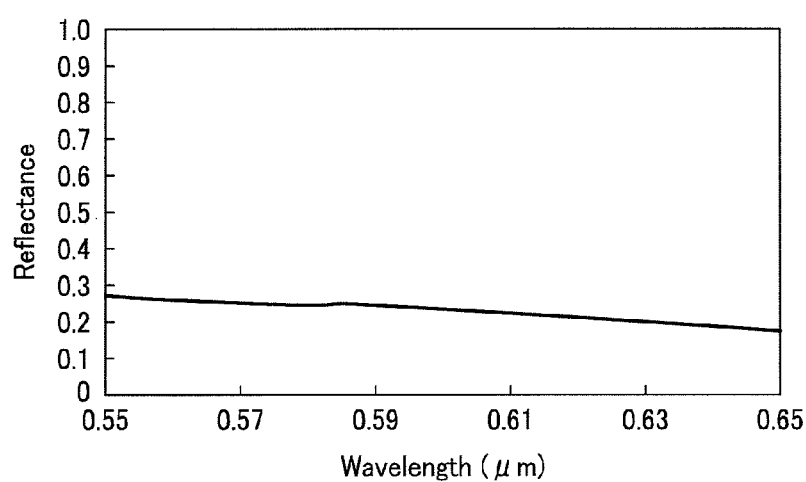
FIG. 44 is a graph for explaining a comparative example 2 of the wavelength selection filter.
Figure 45:
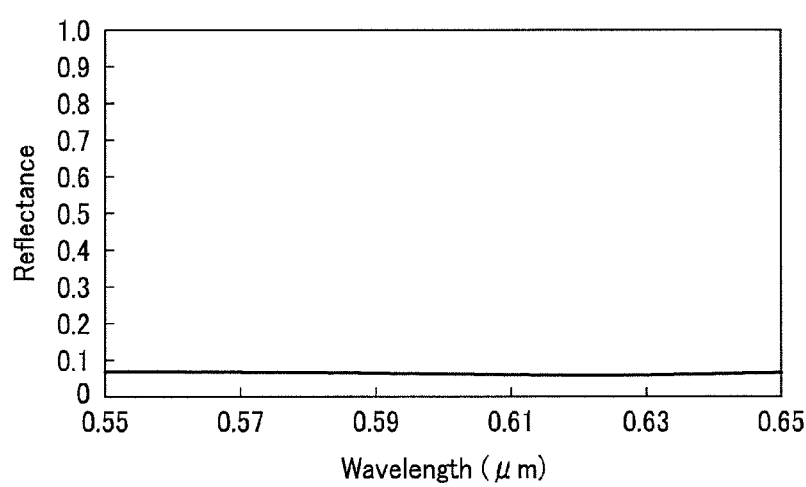
FIG. 45 is a graph for explaining a comparative example 3 of the wavelength selection filter.

Meanwhile, FIG. 43 shows the relationship between the wavelength and reflectance of incident light, which is observed in the case of using the wavelength selection filter having the same structure as the wavelength selection filter 201 and having a transparent film with a refractive index of 1.385. Further, FIG. 44 shows the relationship between the wavelength and reflectance of incident light, which is observed in the case of using the wavelength selection filter having the same structure as the wavelength selection filter 201 and having a transparent film with a refractive index of 1.25. Furthermore, FIG. 45 shows the relationship between the wavelength and reflectance of incident light, which is observed in the case of using the wavelength selection filter having the same structure as the wavelength selection filter 101 and having a transparent film with a refractive index of 1.385. In any of these instances, the refractive index of the transparent film is lower than that of the substrate, which in turn makes it impossible to achieve desired optical properties for the wavelength selection filter.

FIG. 46 shows a table of the structures and optical properties of the wavelength selection filters 101, 201 and 301 and the conventional wavelength selection filter (conventional example).

Incidentally, in the wavelength selection filters 101, 201 and 301, the land width L, the widths t0 to t3 and the refractive indices n0 to n3, as well as the pitch P, may be adjusted thereby to vary the wavelength region of reflected light, and the center wavelength and half-width of the wavelength region. It should be noted, however, that the relationships $n1>n0$, $n2>n0$ need to be satisfied.

Figure 47A:
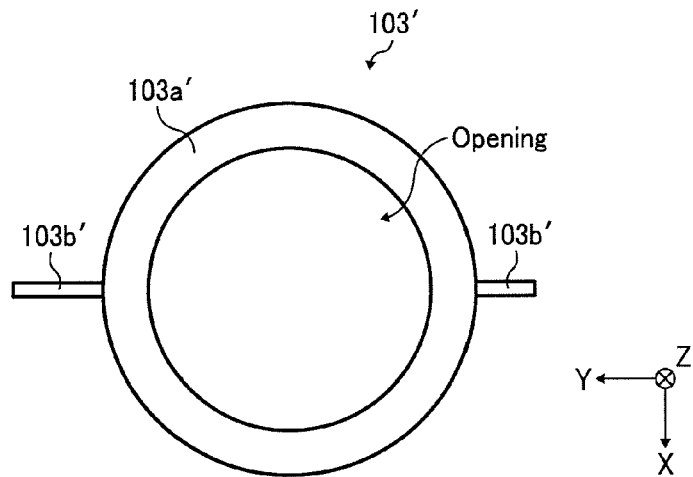
FIGS. 47A to 47C are views for explaining a modified example of the retaining member.
Figure 47B:
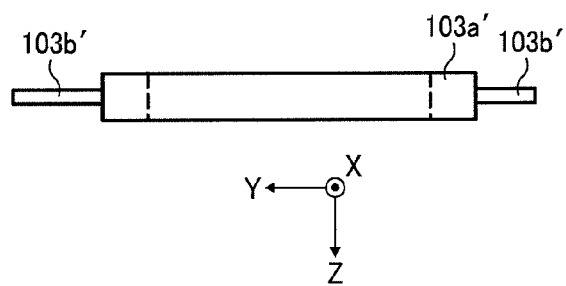
Figure 47C:
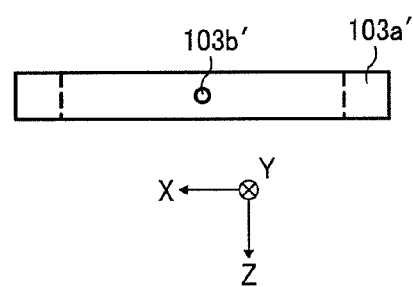

Also, in the embodiment, a retaining member 103' shown in FIGS. 47A to 47C may be used in place of the retaining member 103. The retaining member 103' has a circular opening at its center, and has a doughnut-shaped frame portion (a frame portion 103a'). Such retaining member 103' allows uniform tension distribution from the center of the optical axis toward its outer periphery when being bonded to the wavelength selection filter. Thus, the wavelength selection filter can be bonded to the retaining member 103' without undesired distortion.

Also, in the embodiment, description has been given of an instance where the width t0 of the convex portion, the width t1 of the first layer 101b1, the width t2 of the second layer 101b2, and the width t3 of the third layer 101b3 are equal; however, the present invention is not limited thereto. These values may be changed according to required optical properties (such as the wavelength region of reflected light and the center wavelength and half-width of the wavelength region).

Also, in the embodiment, description has been given of an instance where the material for the first layer 101b1 is the same as that for the second layer 101b2; however, the present invention is not limited thereto. The material for the first layer 101b1 may be different from that for the second layer 101b2, provided that the relationships $n1>n0$ and $n2>n0$ are satisfied.

Also, in the embodiment, description has been given of an instance where quartz ($SiO_2$) is used as the material for the substrate 101a; however, the present invention is not limited thereto. Any material other than quartz ($SiO_2$) may be used as the material for the substrate 101a, provided that the relationships $n1>n0>n3$ and $n2>n0>n3$ are satisfied.

Also, in the embodiment, the concave and convex structure may have a cross section in the form of trapezoids or in the form in which at least one corner of each convex portion and concave portion is chamfered, the cross section being perpendicular to the Y-axis direction.

Also, in the embodiment, if it is not necessary to change the incident angle of light incident on the wavelength selection filter 101, the driving mechanism 105 does not necessarily have to be provided. In this instance, the retaining member 103 is fixed to a housing (not shown) of the light source device 10. Thus, the wavelength region of light outputted from the light source device 10 and the center wavelength of the wavelength region are kept constant.

Incidentally, the use of the light source device 10 in an optical apparatus requiring light lying within a given wavelength range brings desired optical properties without a cost increase.

Also, any one of the wavelength selection filters 101, 201 and 301 may be used in a device including an optical system that receives a light bundle in which multiple light beams of different wavelengths are mixed together, and separates a light beam lying within a given wavelength range from the received light bundle. This enables improvements in characteristics inherent in the device as compared to the conventional case without a cost increase.

Figure 48:
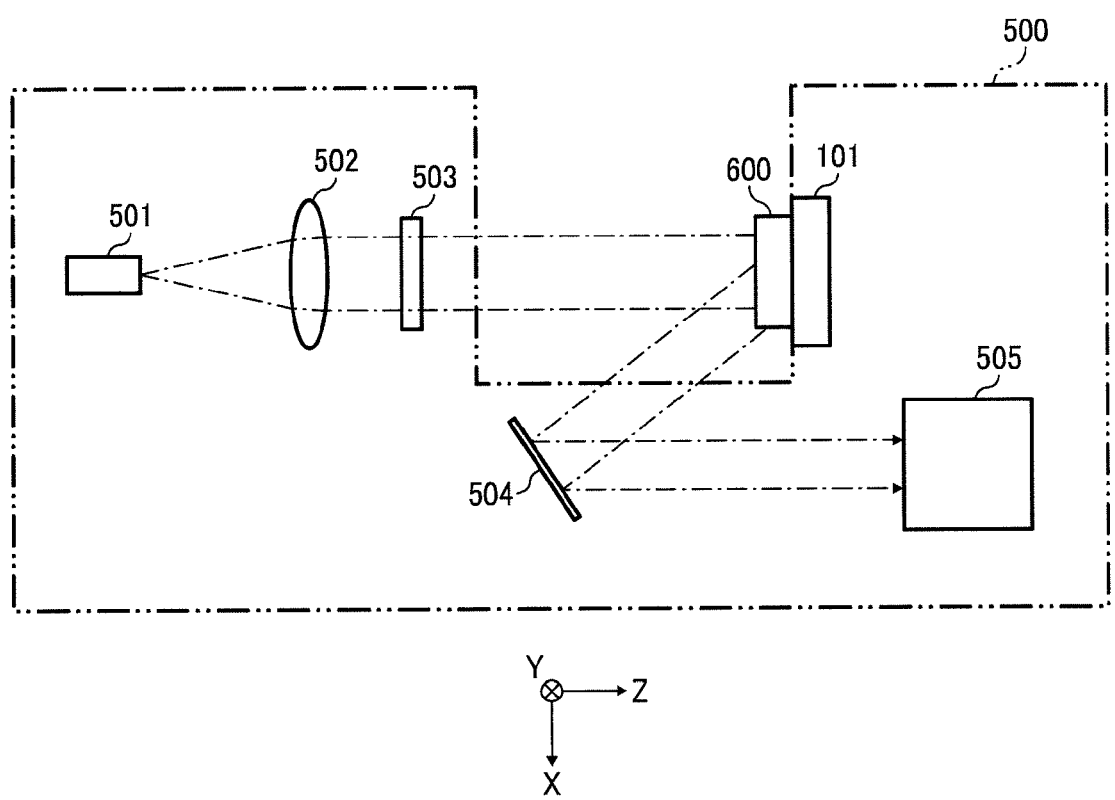
FIG. 48 is a schematic diagram of a refractive index sensor according to the embodiment of the present invention.

FIG. 48 shows a refractive index sensor 500 according to the embodiment of the present invention. The refractive index sensor 500 for detecting a refractive index of a target includes a light source 501, a first optical element such as a coupling lens 502, a second optical element such as an optical element 503, the wavelength selection filter 101, a detector 505, and the like. A target 600 whose refractive index is to be detected is mounted on the refractive index sensor 500 so that the target 600 may be located between the optical element 503 and the wavelength selection filter 101 and may be brought into contact with the wavelength selection filter 101. In an XYZ three-dimensional orthogonal coordinate system in the description herein, the direction of the optical axis of the coupling lens 502 is regarded as the Z-axis direction.

The light source 501 outputs what is called white light. The coupling lens 502 substantially collimates a light bundle outputted from the light source 501. The optical element 503 linearly polarizes the light bundle having passed through the coupling lens 502. The target 600 is irradiated with the light bundle having passed through the optical element 503. Here, the light bundle having passed through the optical element 503 falls incident on the target 600 at an incident angle of 0°.

The wavelength selection filter 101 receives the light bundle having transmitted through the target 600. At this time, the light bundle falls incident on the wavelength selection filter 101 at an incident angle depending on the refractive index of the target 600. Then, the wavelength selection filter 101 selectively reflects a light beam from the light bundle having wavelengths depending on the incident angle. The light beam reflected by the wavelength selection filter 101 falls incident on the detector 505 through a reflecting mirror 504.

The detector 505 has a spectroscope, and uses the spectroscope to obtain the peak wavelength of the incident light beam. Then, the detector 505 obtains the incident angle at which the light beam having transmitted through the target 600 falls incident on the wavelength selection filter 101, on the basis of the peak wavelength. Further, the detector 505 obtains the refractive index of the target 600 from the incident angle thus obtained.

In this manner, the refractive index sensor 500 including the wavelength selection filter 101 is capable of accurately detecting the refractive index of the target without a cost increase.

Incidentally, the wavelength selection filter 201 or 301 may be used in place of the wavelength selection filter 101.

One example of the present invention provides a wavelength selection filter selectively resonating and reflecting light of a given wavelength contained in incident light, including: a substrate being formed on a plane on which the incident light falls incident, and having a concave and convex structure in a rectangular waveform in one axial direction; and a multilayer structure including a first layer and a second layer respectively coating one and the other one of side surfaces, in the one axial direction, of each of convex portions of the concave and convex structure. In the wavelength selection filter, a refractive index of the first layer and a refractive index of the second layer are both higher than a refractive index of the substrate. Such wavelength selection filter is capable of enhancing the wavelength selectivity and widening the allowable range of the incident angle of light.

Another example of the present invention provides a filter unit including: the wavelength selection filter of the present invention; and a rotating mechanism rotating the wavelength selection filter about an axis parallel to a surface of the substrate and perpendicular to the one axial direction.

Thereby, the filter unit including the wavelength selection filter of the present invention is capable of easily reflecting light of a desired wavelength without a cost increase.

Another example of the present invention provides a first light source device including: a light source; an optical element substantially collimating a light bundle from the light source; and the wavelength selection filter of the present invention receiving the light bundle that has passed through the optical element. In the first light source device, a light beam reflected by the wavelength selection filter is outputted.

Another example of the present invention provides, in a fourth aspect, a second light source device including: a light source; an optical element substantially collimating a light bundle from the light source; and the filter unit of the present invention receiving the light bundle transmitted through the optical element. In the second light source device, a light beam reflected by the wavelength selection filter of the filter unit is outputted.

Any of the above-described light source devices has the wavelength selection filter of the present invention, and thus is capable of easily outputting light of a desired wavelength without a cost increase.

Another example of the present invention provides an optical apparatus 30 including: the light source device 10 of the present invention; and an optical system 20 receiving a light beam outputted from the light source device.

Thereby, the optical apparatus including the light source device of the present invention is capable of achieving desired optical properties without a cost increase.

Another example of the present invention provides a refractive index sensor for detecting a refractive index of a target, including: a light source; a first optical element substantially collimating a light bundle from the light source; a second optical element linearly polarizing the light bundle transmitted through the first optical element; the wavelength selection filter of the present invention receiving the light bundle exited from the second optical element and transmitted through the target; and a detector obtaining a peak wavelength of a light beam reflected by the wavelength selection filter, and detecting the refractive index of the target based on the obtained peak wavelength.

Thereby, the refractive index sensor including the wavelength selection filter of the present invention is capable of accurately detecting the refractive index of the target without a cost increase.

As has been described above, the wavelength selection filter of the present invention is suitable for achieving a wider allowable range of the incident angle of light and enhanced wavelength selectivity. The filter unit of the present invention is suitable for easily reflecting light of a desired wavelength without a cost increase. The light source device of the present invention is suitable for easily outputting light of a desired wavelength without a cost increase. The optical apparatus of the present invention is suitable for achieving desired optical properties without a cost increase. The refractive index sensor of the present invention is suitable for accurately detecting the refractive index of a target without a cost increase.

Although the present invention has been described in terms of exemplary embodiments, it is not limited thereto. It should be appreciated that variations may be made in the embodiments described by persons skilled in the art without departing from the scope of the present invention as defined by the following claims.

What is claimed is:

1. A wavelength selection filter selectively resonating and reflecting light of a given wavelength contained in incident light, comprising:
   a substrate having a rectangular waveform concave and convex structure which is formed on a plane on which the incident light falls incident, the concave and convex structure including convex portions and concave portions which are arranged in one axial direction; and
   a multilayer structure including a first layer and a second layer respectively coating one and the other one of side surfaces, in the one axial direction, of each of convex portions of the concave and convex structure,
   wherein a refractive index of the first layer and a refractive index of the second layer are both higher than a refractive index of the substrate,
   wherein the multilayer structure includes a third layer located between the first layer and the second layer in the one axial direction, and
   a refractive index of the third layer is lower than the refractive index of the substrate,
   wherein, in the one axial direction, a width of each convex portion of the concave and convex structure, a width of the first layer, a width of the second layer, and a width of the third layer are equal to one another, and
   wherein the first layer and the second layer are substantially transparent.

2. The wavelength selection filter according to claim 1, wherein the refractive index of the first layer is equal to the refractive index of the second layer.

3. The wavelength selection filter according to claim 1, wherein the refractive index of the first layer is different from the refractive index of the second layer.

4. The wavelength selection filter according to claim 3, wherein the third layer is an air layer.

5. The wavelength selection filter according to claim 1, wherein a height of each convex portion of the concave and convex structure is twice the width of the convex portion in the one axial direction.

6. A filter unit comprising:
   the wavelength selection filter according to claim 1; and
   a rotating mechanism rotating the wavelength selection filter about an axis parallel to a surface of the substrate and perpendicular to the one axial direction.

7. A light source device comprising:
   a light source;
   an optical element substantially collimating a light bundle from the light source; and
   the filter unit according to claim 6 receiving the light bundle transmitted through the optical element,
   wherein a light beam reflected by the wavelength selection filter of the filter unit is outputted.

8. A light source device comprising:
   a light source;
   an optical element substantially collimating a light bundle from the light source; and
   the wavelength selection filter according to claim 1 receiving the light bundle that has passed through the optical element,
   wherein a light beam reflected by the wavelength selection filter is outputted.

9. An optical apparatus comprising:
   the light source device according to claim 8; and
   an optical system receiving a light beam outputted from the light source device.

10. A refractive index sensor for detecting a refractive index of a target, comprising:
    a light source;
    a first optical element substantially collimating a light bundle from the light source;
    a second optical element linearly polarizing the light bundle transmitted through the first optical element;
    a wavelength selection filter receiving the light bundle exited from the second optical element and transmitted through the target; and
    a detector obtaining a peak wavelength of a light beam reflected by the wavelength selection filter, and detecting the refractive index of the target based on the obtained peak wavelength,
    the wavelength selection filter selectively resonating and reflecting light of a given wavelength contained in the light bundle, including:
    a substrate having a rectangular waveform concave and convex structure which is formed on a plane on which the light bundle falls incident, the concave and convex structure including convex portions and concave portions which are arranged in one axial direction; and
    a multilayer structure including a first layer and a second layer respectively coating one and the other one of side surfaces, in the one axial direction, of each of convex portions of the concave and convex structure,
    wherein a refractive index of the first layer and a refractive index of the second layer are both higher than a refractive index of the substrate.

* * * * *